US006225073B1

(12) United States Patent
Alexander et al.

(10) Patent No.: US 6,225,073 B1
(45) Date of Patent: May 1, 2001

(54) IMMUNOASSAY FOR MYCOPHENOLIC ACID

(75) Inventors: Svetlana Alexander, Sunnyvale; Dariush Davalian, San Jose, both of CA (US)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 08/271,876

(22) Filed: Jul. 7, 1994

(51) Int. Cl.$^7$ .......................... G01N 33/535; C12N 9/96; C07K 16/44
(52) U.S. Cl. ................... 435/7.93; 435/188; 436/815; 530/403; 530/404; 530/405; 530/406; 530/388.9; 530/389.8
(58) Field of Search .................... 435/7.93, 188; 530/403, 404, 405, 406, 389.8, 388.9; 436/815

(56) References Cited

U.S. PATENT DOCUMENTS

| 4,753,935 | 6/1988 | Nelson et al. ................ 544/153 |
| 5,284,935 | * 2/1994 | Clark et al. ................ 530/806 |

FOREIGN PATENT DOCUMENTS

18012   * 11/1991   (WO) .

OTHER PUBLICATIONS

Epinette, et al., J. American Academy of Dermatology, (Dec. 1987) vol. 17:6 pp. 962–971 "Mycophenolic acid for psoriasis".

Lee, et al., Pharmaceutical Research, (1990) vol. 7:2 pp. 161–166 "Bioavailability Improvement of Mycophenolic Acid Through Amino Ester Derivatization".
Nelson, et al., J. Medicinal Chemistry, (1990) vol. 33:2 pp. 833–838 "Synthesis and Immunosuppressive Activity of Some Side–Chain Variants of Mycophenoic Acid".
Jones, et al., J. Chem. Soc. (C), (1970) pp. 1725–1735 "Microbial Modification of Mycophenolic Acid".
M. Brinkley, Bioconjugate Chem. vol. 3, pp. 2–13 (1992).*
B. Erlanger, Methods in Enzymology, vol. 70, pp. 85–105 (1980), Academic Press, Inc.*
N. Rose et al., Manual of Clinical Laboratory Immunology, Third Edition, American Society for Microbiology, Washington, D.C. (1986), pp. 99–109.*

* cited by examiner

Primary Examiner—Mary E. Ceperley

(57) ABSTRACT

The present invention provides antibodies useful in assays for mycophenolic acid (MPA). These antibodies bind MPA and are able to distinguish MPA from its esters, such as morpholinoethyl E-6-(1,3-dihydro-4-hydroxy-6-methoxy-7-methyl-3-oxo-5-isobenzofuranyl)-4-methyl-4-hexenoate, and/or its metabolites, such as mycophenolic acid glucuronide. The present invention also provides conjugates of labels and MPA or MPA analogs. The antibodies of the invention are capable of binding these conjugates and are also capable of inhibiting the activity of the label when bound to the conjugates. The present invention also provides methods for the determination of MPA in a sample suspected of containing MPA that use the antibodies and/or conjugates of the invention. The present invention also provides assay reagents as well as packaged kits useful for performing the methods of the invention.

38 Claims, No Drawings

IMMUNOASSAY FOR MYCOPHENOLIC ACID

BACKGROUND OF THE INVENTION

FIELD OF THE INVENTION

Mycophenolic acid ("MPA") is produced by the fermentation of several penicillium species.

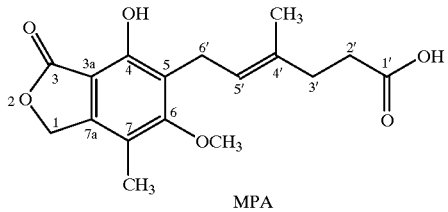

MPA

It has a broad spectrum of activities, specific mode of action, and is tolerable in large doses with minimal side effects, Epinette, et al., *Journal of the American Academy of Dermatology* 17(6):962–71 (1987). MPA has been shown to have antitumor, antiviral, antipsoriatic, immunosuppressive, anti-inflammatory activities, Lee, et al., *Pharmaceutical Research* 7(2):161–166 (1990), along with antibacterial and antifungal activities, Nelson, et al., *Journal of Medicinal Chemistry* 33(2):833–838 (1990). It inhibits inosine monophosphate dehydrogenase, an enzyme in the de novo synthesis of purine nucleotides. Since T and B lymphocytes depend largely upon this de novo synthesis, MPA is able to inhibit lymphocyte proliferation, which is a major factor of the immune response.

The morpholinoethyl ester of MPA, morpholinoethyl E-6-(1,3-dihydro-4-hydroxy-6-methoxy-7-methyl-3-oxo-5-isobenzofuranyl)-4-methyl-4-hexenoate ("MPA-M") is rapidly hydrolyzed in vivo to MPA. Administration of MPA in the form of this ester, greatly improves MPA's bioavailability.

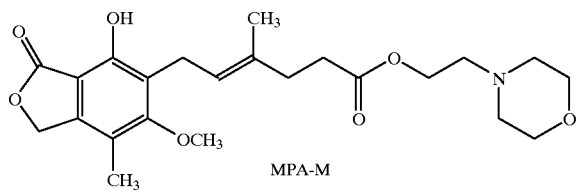

MPA-M

MPA-M has a number of other favorable pharmaceutical characteristics, including its stability at pH 2–5 and its good solubility at low pH indicating rapid dissolution in the upper GI tract, Lee, et al., supra.

When used in combination therapy with cyclosporin A ("CsA"), MPA-M and CsA may have a synergistic mode of action. CsA has a selective effect on T cells, but does not suppress B cell antibody production activity, while MPA has an anti-proliferative effect on both T and B cells. Combined CsA/MPA-M therapy may increase survival time and allow for use of lower doses of CsA, which would reduce the side effects associated with CsA, primarily nephrotoxicity.

Because MPA is a potent biologically active material, an effective immunoassay would be useful in monitoring its bioavailability. In addition, it may be important to monitor therapeutic drug levels, i.e., optimal drug levels necessary for adequate immunosuppression. Since MPA-M is rapidly hydrolyzed to MPA, an assay for MPA would allow monitoring of MPA-M dosages.

Such assays, however, are limited by the difficulty of preparing antibodies which bind specifically to MPA and not to any MPA-M or metabolites such as the inactive metabolite mycophenolic acid glucuronide ("MPA-G"), that may be present.

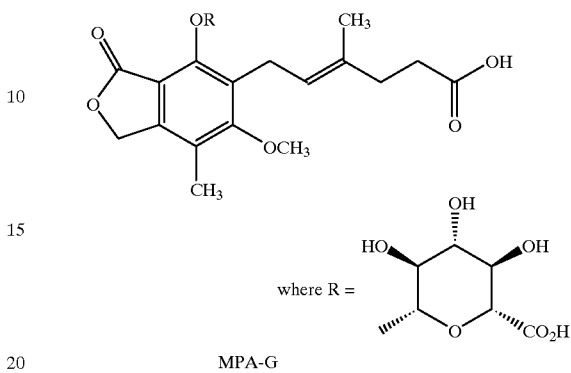

MPA-G

The present invention addresses this need. The present invention provides antibodies that bind MPA and are able to modulate the activity of a label that is bound to another antibody or to an MPA analog and, further, that are capable of distinguishing between MPA and cross-reactive materials such as mycophenolate esters and/or MPA metabolites.

DESCRIPTION OF THE RELATED ART

Jones, et al., *J. Chem. Soc.* (C) 1725–1737 (1970) discloses numerous transformations that mycophenolic acid undergoes when incubated with select microorganisms.

Nelson, et al., U.S. Pat. No. 4,753,935, pertains to MPA-M, its pharmaceutical uses, and post-dosage monitoring by HPLC of the recipient's plasma concentration of MPA.

SUMMARY OF THE INVENTION

The present invention relates to a method for the determination of mycophenolic acid ("MPA") in a sample suspected of containing MPA comprising the steps of: (a) contacting the sample with an antibody capable of distinguishing between MPA and mycophenolate esters; and (b) detecting the binding of the antibody to MPA. This method can be homogeneous or heterogeneous. Alternatively, this method uses an antibody capable of distinguishing between MPA and MPA metabolites.

Another aspect of the present invention relates to a method for measuring the amount of MPA in a sample suspected of containing MPA which comprises the steps of: (a) combining in an aqueous medium: the sample, MPA conjugated to a detectable label, and an antibody capable of distinguishing between MPA and a compound selected from the group consisting of mycophenolate esters and mycophenolic acid metabolites; and (b) determining the effect of the sample on the activity of the label.

Another aspect of the present invention relates to a method for homogeneous immunoassay of MPA in a sample suspected of containing this analyte which comprises: (a) combining in a liquid medium: the sample, a conjugate of an MPA analog and an enzyme, an antibody capable of distinguishing between MPA and mycophenolate esters, and substrates for the enzyme; (b) determining the enzymatic activity of the enzyme in the medium; and (c) comparing the activity to the enzymatic activity observed with a sample containing a known amount of the analyte. Alternatively, this method uses an antibody capable of distinguishing between MPA and MPA metabolites.

Another aspect of the present invention relates to a compound comprising MPA bound to a protein by replacement of one or more hydrogen atoms. This invention also relates to an antibody raised in response to this compound, which is capable of distinguishing between MPA and a compound selected from the group consisting of mycophenolate esters and MPA metabolites. The antibody can be bound to a detectable label.

Yet another aspect of the invention relates to a kit for conducting an assay for the determination of MPA, comprising in packaged combination: an antibody capable of distinguishing between MPA and mycophenolate esters, and a compound comprising MPA bound to a detectable label. Alternatively, this kit uses an antibody capable of distinguishing between MPA and MPA metabolites.

DESCRIPTION OF THE SPECIFIC EMBODIMENTS

Before proceeding with the description of the specific embodiments of the invention, a number of terms will be defined.

Sample suspected of containing the analyte: any sample which is reasonably suspected of containing the analyte, i.e., MPA, can be analyzed by the method of the present invention. The sample is typically an aqueous solution such as a body fluid from a host, for example, urine, whole blood, plasma, serum, saliva, semen, stool, sputum, cerebral spinal fluid, tears, mucus, or the like, but preferably is plasma or serum. The sample can be pretreated as described below and can be prepared in any convenient medium which does not interfere with the assay. An aqueous medium is preferred.

Interfering cross-reactive material: material other than MPA that may be recognized by antibodies that bind MPA is an interfering cross-reactive material. These include compounds related to MPA, such as mycophenolate esters and MPA metabolites. The term "mycophenolate ester" includes, but is not limited to, esters of MPA at the carboxylic acid group of the side chain attached at the 1' position of the MPA isobenzofuranyl ring system such as MPA-M. The term "MPA metabolite" refers to the products of the metabolism of MPA, preferably products containing the isobenzofuranyl ring system, more preferably products also containing a portion of the side chain attached at position 1', such as MPA-G.

Measuring the amount of MPA: quantitative, semiquantitative, and qualitative methods as well as all other methods for determining MPA are considered to be methods of measuring the amount of MPA. For example, a method which merely detects the presence or absence of MPA in a sample suspected of containing MPA is considered to be included within the scope of the present invention. The terms "detecting" and "determining", as well as other common synonyms for measuring, are contemplated within the scope of the present invention.

Capable of distinguishing between: the ability of a receptor or antibody to bind preferentially to a first ligand relative to a second ligand. In the present invention, the first ligand is MPA and the second ligand is a mycophenolate ester or MPA metabolite. Usually at least 5-fold more of the first ligand than the second ligand will be bound when the antibody is combined with a sample containing the ligands. Preferably, at least 10-fold more and, more preferably, at least 20-fold more of the first ligand will be bound. Although the relative binding of each ligand will depend on the relative concentrations in the sample, usually these conditions are met when the binding constant of the antibody to the first ligand is at least equal to the binding constant to the second ligand, and, preferably, is at least 10-fold, more preferably, at least 50-fold the binding constant to the second ligand. The cross-reactivity of an antibody to a first ligand refers to the ratio of the concentration of the first ligand to that of the second ligand that causes the two ligands to be bound in equal amounts. Quantification of a "high" or "low" degree of cross-reactivity, i.e., the extent of cross-reactivity that is acceptable, depends on the highest concentration expected of the cross-reactant, the sensitivity required for the assay and the accuracy needed. For example, if an antibody is 10% cross-reactive with MPA-G and MPA-G is present in a sample in an amount five times greater than the lowest level of MPA to be detected, then the measured level of MPA will be 50% too high when MPA is at its lowest level. If only a 5% error is acceptable, then the cross-reactivity would have to be less than 1%. In the present invention, antibodies directed against MPA must exhibit a low degree of cross-reactivity with materials such as MPA-M and MPA-G.

Conjugate: a molecule comprised of two or more molecules bound together, optionally through a linking group, to form a single structure. The binding can be made either by a direct connection (e.g. a chemical bond) between the molecules or by use of a linking group. For example, in one context of the present invention, an MPA analog conjugated to an enzyme is an MPA analog-enzyme conjugate.

Member of a specific binding pair ("sbp" member): one of two different molecules having an area on the surface or in a cavity that specifically binds to and is therefore defined as complementary with a particular spatial and polar organization of the other molecule. The members of the sbp can be referred to as ligand and receptor such as members of an immunological pair, e.g., antigen-antibody. As used herein, the term "ligand" refers to any organic compound for which a receptor naturally exists or can be prepared and the term "receptor" refers to any compound or composition capable of recognizing a particular spatial and polar organization of a molecule, i.e., epitopic or determinant site. Complementary sbp members bind to one another, as for example, a ligand and its complementary receptor. Sbp members can be immunological pairs such as antigen and antibody, or non-immunological pairs such as avidin and biotin. Sbp members can also be small molecules or residues of small molecules and their receptors. Small molecules have a molecular weight of from 100–2000, preferably 150–1000, and a receptor for the small molecule either exists or can be prepared. Examples of small molecules include derivatives of biotin, lysergic acid, fluorescein or a fluorescein derivative, and vitamin $B_{12}$, with the corresponding receptors being avidin or streptavidin, anti-lysergic acid, anti-fluorescein and intrinsic factor, respectively. Small molecules are often covalently bound to other sbp members to form a conjugate having at least one, and frequently 2–20, small molecules. Bonding of the small molecule to the sbp member may be accomplished by chemical reactions which result in replacing a hydrogen atom of the small molecule with a bond to the sbp member or by a linking group between the small molecule and the sbp member of any size but preferably no larger than necessary to permit binding to the conjugate of both a receptor for the small molecule and the sbp member.

Hapten: a compound capable of binding specifically to corresponding antibodies, but do not themselves act as immunogens (or antigens) for preparation of the antibodies.

Antibodies which recognize a hapten can be prepared against compounds comprised of the hapten linked to an immunogenic (or antigenic) carrier. Haptens are a subset of ligands.

MPA analog: modified MPA. The modification provides means to join this analog to another molecule. The analog will usually differ from MPA by more than replacement of a hydrogen with a bond which links the analog to a hub or label.

Immunogenic carrier: a group which, when conjugated to a hapten and injected into a mammal, will induce an immune response and elicit the production of antibodies that bind to the hapten, in this case MPA. Immunogenic carriers are also referred to as antigenic carriers. Typical immunogenic carriers include, without limitation, poly(amino acids), polysaccharides, nucleic acids and particles (biologic and synthetic materials). A wide variety of such carriers are disclosed in Davalian, et al., U.S. Pat. No. 5,089,390, column 4, line 57 to column 5, line 5, incorporated herein by reference. Other suitable immunogenic carriers include albumins, serum proteins, e.g., globulins, ocular lens proteins and lipoproteins. Illustrative proteins include bovine serum albumin, keyhole limpet hemocyanin ("KLH"), egg ovalbumin and bovine gamma-globulin.

Support or surface: The solid phase is typically a support or surface, which is a porous or non-porous water insoluble material that can have any one of a number of shapes, such as strip, rod, particle or beads. A wide variety of suitable supports are disclosed in Ullman, et al. U.S. Pat. No. 5,185,243, columns 10–11, Kurn, et al., U.S. Pat. No. 4,868,104, column 6, lines 21–42 and Milburn, et al., U.S. Pat. No. 4,959,303, column 6, lines 14–31, which are incorporated herein by reference. Binding of sbp members to a support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970).

Signal producing system ("sps"): one or more components, at least one component being a detectable label, which generate a detectable signal that relates to the amount of bound and/or unbound label, i.e. the amount of label bound or not bound to the compound being detected. The label is any molecule that produces or can be induced to produce a signal, and preferably is a fluorescer, radiolabel, enzyme, chemiluminescer or photosensitizer. Thus, the signal is detected and/or measured by detecting enzyme activity, luminescence, light absorbance or radioactivity.

Suitable labels include, by way of illustration and not limitation, enzymes such as alkaline phosphatase, glucose-6-phosphate dehydrogenase ("G6PDH") and horseradish peroxidase; ribozyme; a substrate for a replicase such as QB replicase; promoters; dyes; fluorescers, such as fluorescein, isothio-cyanate, rhodamine compounds, phycoerythrin, phycocyanin, allophycocyanin, o-phthaldehyde, and fluorescamine; chemiluminescers such as isoluminol; sensitizers; coenzymes; enzyme substrates; radiolabels such as $^{125}$I, $^{131}$I, $^{14}$C, $^{3}$H, $^{57}$Co and $^{75}$Se; particles such as latex or carbon particles; metal sol; crystallite; liposomes; cells, etc., which may be further labeled with a dye, catalyst or other detectable group. Suitable enzymes and coenzymes are disclosed in Litman, et al., U.S. Pat. No. 4,275,149, columns 19–28, and Boguslaski, et al., U.S. Pat. No. 4,318,980, columns 10–14; suitable fluorescers and chemiluminescers are disclosed in Litman, et al., U.S. Pat. No. 4,275,149, at columns 30 and 31; which are incorporated herein by reference.

There are numerous methods by which the label can produce a signal detectable by external means, desirably by visual examination, for example by electromagnetic radiation, heat, and chemical reagents. The label or other sps members can also be bound to an sbp member, another molecule or to a support.

The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal, which may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al. U.S. Pat. No. 5,185,243, columns 11–13, incorporated herein by reference.

The label can be bound covalently to numerous sbp members: an antibody that binds MPA; a receptor for an antibody that binds MPA; a receptor that is capable of binding to a small molecule conjugated to an antibody that binds MPA; or a ligand such as an MPA analog. Bonding of the label to the sbp member may be accomplished by chemical reactions which result in replacing a hydrogen atom of the label with a bond to the sbp member or may include a linking group between the label and the sbp member. Other sps members may also be bound covalently to sbp members. For example, two sps members such as a fluorescer and quencher can each be bound to a different antibody that forms a complex with the MPA analyte. Formation of the complex brings the fluorescer and quencher in close proximity, thus permitting the quencher to interact with the fluorescer to produce a signal. Methods of conjugation are well known in the art. See for example, Rubenstein, et al., U.S. Pat. No. 3,817,837, incorporated herein by reference. This invention also contemplates having an antibody bound to a first sps member and a detectable label as the second sps member. For example, when the detectable label is bound to an MPA analog, the extent of binding of the antibody to the analog can be measured by detecting the signal produced by the interaction of the sps members.

Ancillary Materials: Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

Linking Group: a portion of a structure which connects 2 or more substructures. The linking group can be a bond or it can have at least 1 uninterrupted chain of atoms other than hydrogen (or other monovalent atoms) extending between the substructures. The number of atoms in the chain will be at least one and is determined by counting the number of atoms other than hydrogen along the shortest route between the substructures being connected, and is typically 1–30, usually 2–10, preferably 3–8, atoms each independently selected from the group consisting of carbon, oxygen, nitrogen, sulfur and phosphorous. The number of total atoms in the linking group is determined by counting the total carbon, oxygen, nitrogen, sulfur and phosphorous atoms, i.e. the atoms other than hydrogen. Typically, the linking group has a total of less than 30 atoms, preferably less than 20 atoms, more preferably less than 10 atoms. As a general rule, the length of a particular linking group can be selected arbitrarily to provide for convenience of synthesis and the incorporation of any desired group. The linking groups may be aliphatic or aromatic, although with diazo groups, aromatic groups will usually be involved. Oxygen will normally be present as oxo or oxy, bonded to carbon, sulfur, nitrogen or phosphorous; nitrogen will normally be present as nitro, nitroso or amino, normally bonded to carbon, oxygen, sulfur or phosphorous; sulfur would be analogous to oxygen; while phosphorous will be bonded to carbon, sulfur, oxygen or nitrogen, usually as phosphonate and phosphate mono- or diester.

Common functionalities in forming a covalent bond between the linking group and the molecule to be conjugated are alkylamine, amidine, thioamide, dithiol, ether, urea, thiourea, guanidine, azo, thioether and carboxylate, sulfonate, and phosphate esters, amides and thioesters.

Lower alkyl: an alkyl group (monovalent branched or unbranched radical derived from an aliphatic hydrocarbon by removal of one H atom) containing from 1–5 carbon atoms. Illustrative examples include methyl, ethyl, propyl, butyl, isopropyl, isobutyl, pentyl and isopentyl.

SPECIFIC EMBODIMENTS

One aspect of the present invention relates to a compound comprising mycophenolic acid ("MPA") bound to a polypeptide, preferably a protein, by replacement of one or more hydrogen atoms, such as a hydrogen atom of the carboxylate group. This compound finds utility as an assay reagent for use in methods of detecting MPA when, for example, the protein is an enzyme label. This compound also finds utility in raising antibodies when, for example, the protein is an immunogenic carrier.

Enzyme and immunogenic carrier conjugates of the invention can be prepared by single or multi-step synthesis, of which numerous standard methods are well known in the art. Typically, such conjugates are prepared by a single step direct coupling of an MPA analog to an enzyme or immunogenic carrier, such as in Scheme I. Alternatively, conjugates are prepared by multi-step synthesis where an MPA analog is first prepared and then linked to the enzyme or immunogenic carrier, such as in Scheme II.

A convenient starting material for such an approach is MPA itself. Typically, MPA is modified at an existing functional group to allow linking or attachment. Preferred functional groups are the phenolic hydroxy at position 4 and the carboxyl group at position 1', more preferably the carboxyl group. For example, modification of the 1' carboxyl functional group by replacement of the hydrogen atom of the carboxylate group yields a compound of the formula:

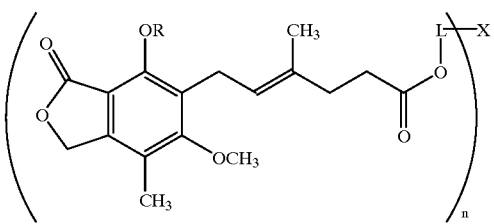

where X is a polypeptide, L is a bond or a linking group, R is H, lower alkyl, or CO-lower alkyl, and n is a number from 1 up to the molecular weight of X divided by 5000.

Exemplary of a single step synthesis of an MPA conjugate utilizing an existing functional group is the method shown in Scheme I:

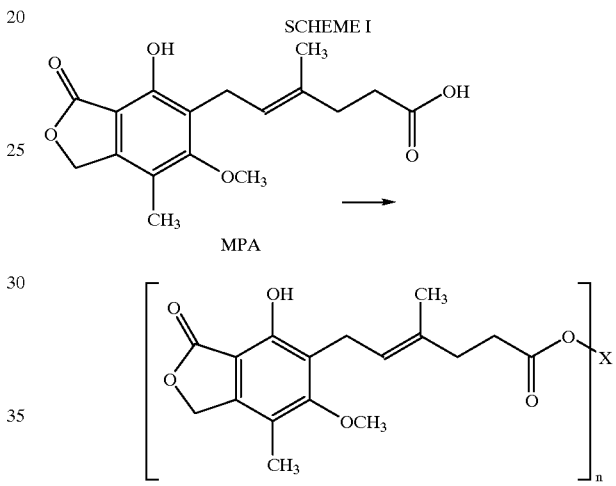

In one approach, Scheme I involves reacting MPA with a compound such as disuccinyl carbonate ("DSC") and an enzyme label or immunogenic carrier in a suitable buffer. Exemplary enzymes include G6PDH and alkaline phosphatase and exemplary immunogenic carriers include KLH. This is an exemplary method intended to illustrate and not to limit the scope of the invention.

Alternatively, a functional group can be added to the MPA structure by oxidation of any C-H bond to form, for example, a hydroxy, aldehyde, ketone, carboxyl, amino, halo or sulfhydryl. More preferably, the oxidation will result in an oxygen containing group such as a hydroxy, aldehyde, ketone, or carboxyl group, still more preferably, a hydroxy group.

Preferably, the oxidation is carried out at a site which is chemically oxidizable in high yield and results in an analog which, when conjugated to an enzyme, yields a conjugate having high inhibitability and modulatability when used in conjunction with an antibody of the invention, and, when conjugated to an immunogenic carrier, results in an immunogen useful in preparing the antibodies of the invention. A preferred site for such an oxidation is the benzylic hydrogens of the methyl group at position 7 of the isobenzofuranyl ring of mycophenolic acid, which yields a compound of the formula:

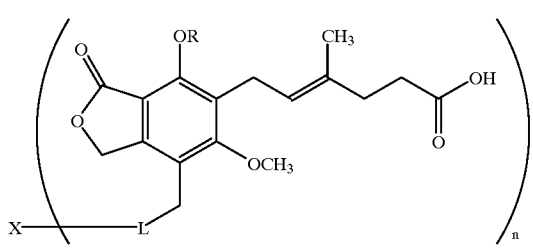

where: X is a polypeptide, L is a bond or a linking group, R is H, lower alkyl, or CO-lower alkyl, and n is a number from 1 up to the molecular weight of X divided by 5000.

Exemplary of a multi-step synthesis based on the oxidative addition of a hydroxy group to mycophenolic acid is the method shown in Scheme II:

SCHEME II

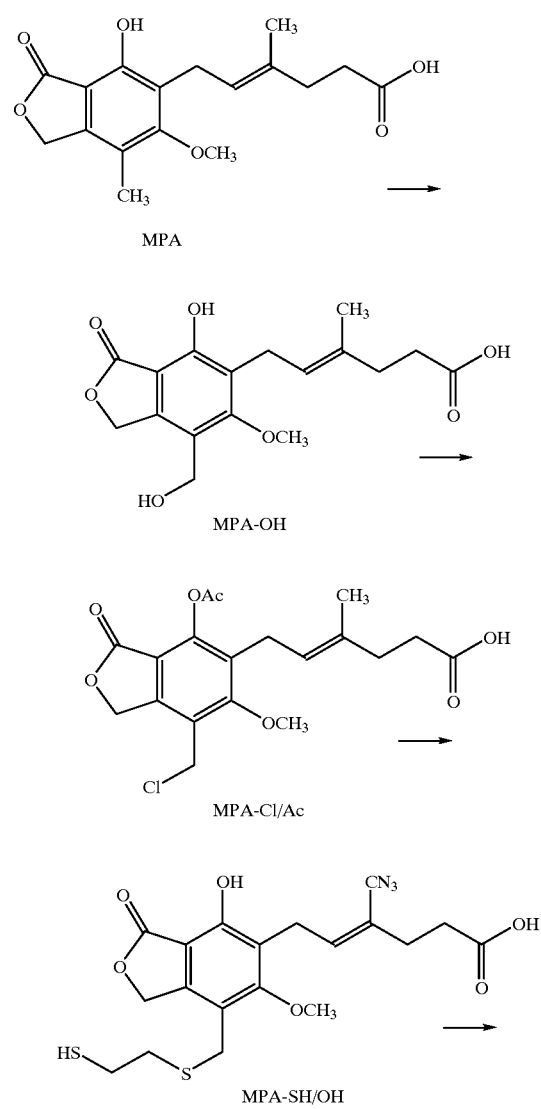

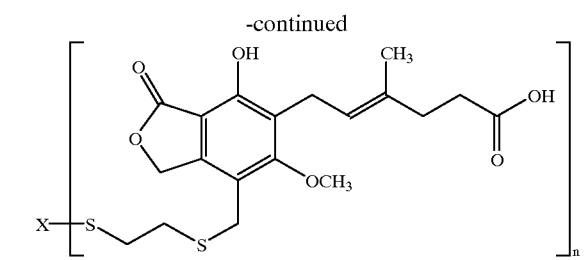

In one approach, Scheme II involves the oxidation of MPA using a modification of the method of Jones, et al., *J. Chem. Soc.* (C) 1725–1737 (1970). MPA is oxidized with alkaline potassium ferricyanide. The resulting compound is treated with acetyl chloride to give chloromethyl MPA, which is then treated with excess 1,2-ethanedithiol in the presence of potassium carbonate to give dithiol extended MPA.

In another alternative approach, a functional group can be added to the MPA structure by modifying an existing functional group, as opposed to oxidation of a C-H bond. By way of example, the methoxy group at position 6 of the isobenzofuranyl ring system is cleaved and the resulting phenolic OH is reacted to form an ether, ester, carbonate, or the like. Preferably, the phenolic OH is reacted to form an ether linkage, wherein the ether group becomes a functional group capable of reacting in a conjugation reaction. This yields a compound of the formula:

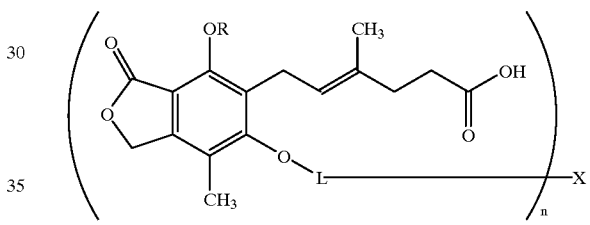

where: X is a polypeptide, L is a bond or a linking group, R is H, lower alkyl, or CO-lower alkyl, and n is a number from 1 up to the molecular weight of X divided by 5000.

Exemplary of a multi-step synthesis based on the modification of an existing functional group is the method shown in Scheme III:

SCHEME III

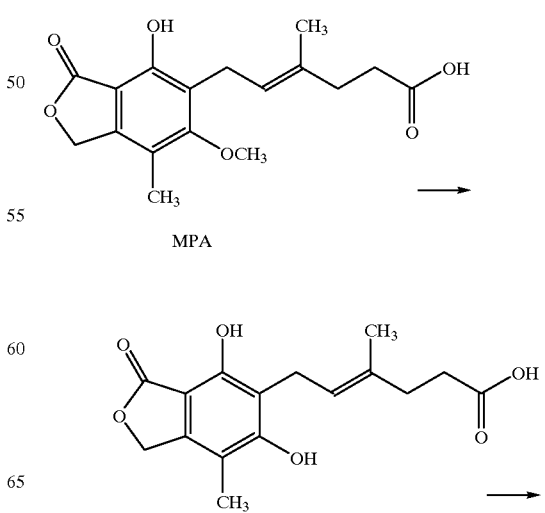

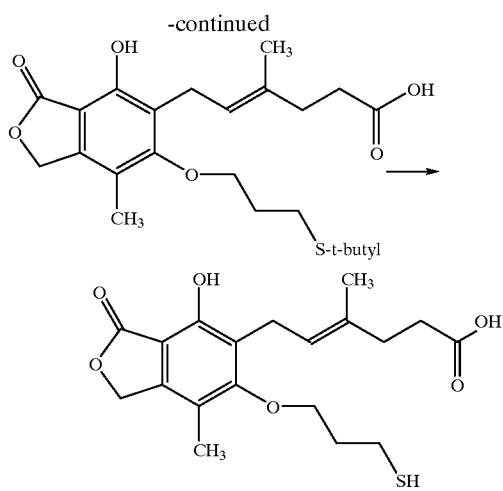

In one approach, Scheme III involves cleavage of the methoxy group at position 6 of the isobenzofuranyl ring by the method described in Harrison, *Chem. Commun.* 16 (1969), by reaction with LiI in collidine. The resulting diphenolic MPA is extended, for example, by the method described in Jones, et al. *Journal of Medicinal Chemistry* 14:305 (1971), by reaction with $K_2CO_3$ and $ICH_2CH_2CH_2S$ (t-bu) in acetone. After optional silica gel chromatography, the protected thiol is deprotected by reaction, for example, with trifluoroacetic acid. Conjugates of dithiol extended MPA are prepared by reaction in phosphate buffer with bromoacetyl modified label enzymes or immunogenic carriers, such as bromoacetyl-KLH or bromoacetyl-G6PDH. This is an exemplary method intended to illustrate and not to limit the scope of the invention. Any of the applicable conjugation methods described above are suitable in the conjugation step of this exemplary methods.

Frequently, the polypeptide will contain an amino or hydroxy group to which the MPA or MPA analog are to be linked and the conjugation step can be any of the numerous standard methods of synthesizing poly(amino acid)s. A summary of such steps can be found in White, et al. "Principles of Biochemistry" (McGraw-Hill, NY, 1978), pages 92–95 of which are incorporated herein by reference. See also, Maggio, E. T. "Enzyme-Immunoassay" (CRC Press, Boca Raton, Fla., 1980), Chapter 4, pages 81–86 of which are incorporated herein by reference.

Generally, when the MPA or MPA analog contains a carboxylate group, any amino, hydroxyl, carboxyl, or other groups which are not to be reacted are protected. This is described in detail in Greene, T. W. "Protective Groups in Organic Synthesis" (Wiley-Interscience, NY, 1981) and McOmie, J. F. W., Ed. "Protective Groups In Organic Chemistry" (Plenum Press, NY, 1973), the relevant portions of which are incorporated herein by reference. Suitable protecting groups include, without limitation, benzyloxycarbonyl, triphenylmethyl, tertiary butyloxycarbonyl, phthaloyl, trifluoroacetyl, benzyl, p-toluenesulfonyl, saturated lower alkyl, benzyl ester, tertiary butyl ester and acetyl.

The optionally protected MPA or MPA analog is then activated. Preferably, the compound will be activated by reaction with an activating reagent such as an alkyl (of less than 9 carbon atoms) chloroformate, e.g. isobutyl-chloroformate; dialkylcarbodiimide, e.g. dicyclohexyl-carbodiimide; 1-ethyl-3-(3-dimethylamino propyl) carbodiimide ("EDAC"), 1-cyclohexyl-3-(2-morpholino-4-ethyl) carbodiimide methyl-p-toluenesulfonate, N-hydroxysuccinimide/EDAC and N-hydroxysulfosuccinimide/ EDAC, in an organic solvent such as dimethyl formamide ("DMF"). The activation reaction is typically carried out at ⁻10–100° C., preferably at 0–30° C., more preferably at 0–10° C., preferably, under an atmosphere of nitrogen, helium, argon, or the like. The activation reaction is carried out for 1 minute to 10 days, preferably from 1 hour to 2 days, more preferably for 6–18 hours.

After the activation reaction, the activated compound is added to a solution of the polypeptide in an organic or aqueous/organic solvent such as DMF or DMF/borate buffer. The addition can take place over a period of time or it may be performed in one step. If the addition takes place over a period of time, it will typically require from 1 minute to 12 hours, preferably from 10 minutes to 8 hours, and more preferably from 30 minutes to 3 hours. After addition, the mixture is allowed to stir for from 1 minute to 3 days, preferably from 10 minutes to 1 day, more preferably from 1–18 hours.

Any unwanted protecting groups can then be removed. The deprotection step will be selected based upon the protecting group detailed above. The above cited references describe conditions and reagents for removal of preferred protecting groups.

Another conjugation method involves reaction of a non-oxo carbonyl functionality of the enzyme or immunogenic carrier with an α-halo or an α-pseudohaloalkylcarbonyl containing compound. The resulting halo or α-pseudohalo containing enzyme or immunogenic carrier is then reacted with a mercaptan containing MPA or MPA analog to form the desired conjugate. This method is disclosed generally in Rowley, et al., U.S. Pat. No. 4,220,722, incorporated herein by reference. The preferred compounds are α-bromo compounds such as α-bromoacetic acid.

Conjugation reactions with enzyme polypeptides, such as G6PDH, can be affected by a number of factors including, but not limited to, pH, temperature, buffer, ionic strength, substances that may protect the enzyme active site, amount and type of cosolvent, reaction time, and activation chemistry. For each enzyme-MPA combination, appropriate manipulation of these variables can lead to conjugates which are improved in one or more of the following properties: reduced deactivation for a given amount of inhibition; larger standard curve; improved assay precision; and enhanced thermal stability. A range of pH values from 5–9.5 can usually be used for conjugation reactions. These reactions are generally carried out at 0–40° C., preferably 4–20° C. A number of buffers and salts, both alone and in combination, can be used for such reactions. These include Tris, bicarbonate, phosphate, pyrophosphate, EDTA, KCl, NaCl, and many others. The active site may be protected by substrates (i.e. G6P), cofactors ($NAD^+$, NADH, $NADP^+$, NADPH) and cofactor analogs (thio-$NAD^+$,thio-NADH, thio-$NADP^+$, or thio-NADPH), and compounds which react reversibly with lysine (i.e. pyridoxal) to reduce deactivation of the enzyme during conjugation. Cosolvents which may enhance MPA solubility include, without limitation, dimethylformamide, carbitol, dimethyl sulfoxide, 1-methyl-2-pyrrolidinone, and 1,3-dimethyl-3,4,5,6-tetrahydro 2(1H)-pyrimidinone. These may be useful as 1–30% of the reaction volume. Reactions can vary from 15 minutes to many days, depending on the activation chemistry. Carboxylic compounds may be activated to form esters with N-hydroxysuccinimide or its sulfo-analog, or to mixed anhydrides through reaction with carbitol chloroformate or t-butylchloroformate, or may be coupled directly using carbodiimides such as EDAC. For reaction with cysteine thiols on the enzyme, MPA or the MPA analog should contain a good leaving group such as I, Br or tosyl; alternatively, MPA or the MPA analog can contain a thiol, activated with a compound such as 2,2' dithio-dipyridine.

The conjugate can be purified if desired. Purification and characterization of poly(amino acid)-hapten conjugates has been disclosed in detail Maggio, supra, Chapter 4, pages 86–88 of which are incorporated herein by reference. For example, purification can be by dialysis against aqueous/organic and aqueous solutions such as water/DMF or water, or by gel filtration chromatography on supports such as Sephadex.

One aspect of the present invention relates to antibodies prepared in response to an immunogen comprising mycophenolic acid ("MPA") or an MPA analog conjugated, optionally through a linking group, to an immunogenic carrier. Furthermore, the present invention includes compounds that are conjugates of such antibodies and a detectable label.

The antibodies of the present invention can be monoclonal or polyclonal and can be prepared by techniques that are well known in the art such as immunization of a host and collection of sera from which the immunoglobulin can be separated by known techniques (polyclonal), by preparing continuous hybrid cell lines and collecting the secreted protein (monoclonal) or by cloning and expressing nucleotide sequences or mutagenized versions thereof coding at least for the amino acid sequences required for specific binding of natural antibodies. Antibodies may include a complete immunoglobulin, or fragment thereof, which immunoglobulins include the various classes and isotypes, such as IgA, IgD, IgE, IgG1, IgG2a, IgG2b and IgG3 and IgM. Fragments thereof may include Fab, Fv, F(ab')2 and Fab.

Monoclonal antibodies can be obtained by the process discussed by Milstein and Kohler in *Nature* 256:495–7 (1975). The host, usually a mouse, is injected with an immunogen, followed by removal of cells from the spleen of the animal. The host may also be unsensitized spleen cells, which are sensitized to the immunogen in vitro. The resulting cells are fused with myeloma cells. The result is a hybrid cell, referred to as a "hybridoma" that can be cultured in vitro. The population of hybridomas is screened and manipulated so as to isolate individual clones, each of which secretes a single antibody to the antigen.

An antibody is an immunoglobulin which specifically binds to and is thereby defined as complementary with a particular spatial and polar organization of another molecule. The antibodies of the present invention are capable of specifically recognizing and binding to MPA, and are therefore useful in assays to detect the presence of MPA in a sample suspected of containing MPA. More importantly, these antibodies are capable of distinguishing between MPA and closely related compounds that may also be present in the sample being assayed, such as those selected from the group consisting of mycophenolate esters and MPA metabolites. In one embodiment of the invention, the antibodies are capable of distinguishing between MPA and mycophenolate esters, such as MPA-M. In another embodiment of the invention, the antibodies are able to distinguish between MPA and MPA metabolites, such as MPA-G.

The antibodies of this invention are preferably raised to an immunogen selected from the group consisting of:

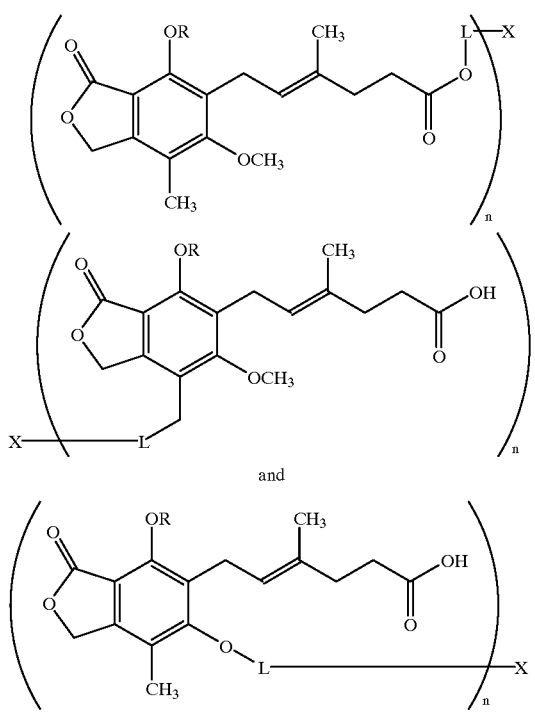

and where X is an immunogenic carrier, L is a bond or a linking group, R is selected from the group consisting of H, lower alkyl, and CO-lower alkyl, and n is a number from 1 up to the molecular weight of X divided by 5000.

As noted above, these antibodies are useful in assays for MPA. Accordingly, another aspect of the present invention relates to methods for the determination of MPA in a sample suspected of containing MPA comprising the steps of: (a) contacting the sample with an antibody capable of distinguishing between MPA and mycophenolate esters; and (b) detecting the binding of the antibody to MPA. Another embodiment of the invention uses an antibody capable of distinguishing between MPA and an MPA metabolite.

This method can further comprises contacting the sample with a labeled analog of MPA in step (a). The method can be homogeneous or heterogeneous. An example of a homogeneous format is where the label is an enzyme whose activity is modified when the antibody binds to the analog. An example of a heterogenous format is where the antibody is bound to a support or capable of being bound to a support. As used herein, the term "capable of being bound to a support" means for example, that a reagent, such as the anti-MPA antibody, is bound to a first sbp member or a small molecule and a complementary second sbp member or receptor for the small molecule, is in turn bound a support. Alternately, a receptor for the anti-MPA antibody, such as an anti-mouse antibody, is bound to a support and used to capture the anti-MPA antibody. Therefore, the anti-MPA antibody is not actually bound to a support, but will become bound, when a complementary sbp member or receptor is added.

The binding of the antibody to MPA can be detected in numerous ways that are well known in the art. Binding of the antibody and MPA forms an immune complex that can be detected directly or indirectly. The immune complexes are detected directly, for example, when the antibodies employed are conjugated to a label. The immune complex is detected indirectly by examining for the effect of immune complex formation in an assay medium on a signal producing system or by employing a labeled receptor that specifically binds to an antibody of the invention.

The assay of the invention has application to all immunoassays for MPA. The assay can be performed either without separation (homogeneous) or with separation (heterogeneous) of any of the assay components or products. Homogeneous immunoassays are exemplified by enzyme multiplied immunoassay techniques ("EMIT") disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59 to column 23, line 25; enzyme channeling techniques such as those disclosed in Maggio, et al., U.S. Pat. No. 4,233,402, column 6, line 25 to column 9, line 63; and other enzyme immunoassays such as the enzyme linked immunosorbant assay ("ELISA") are discussed in Maggio, E. T. supra. Exemplary of heterogeneous assays are the radioimmunoassay, disclosed in Yalow, et al., *J. Clin. Invest.* 39:1157 (1960). The above disclosures are all incorporated herein by reference.

The sample, preferably in a suitable medium, can be examined directly or may be pretreated before the sample is added to the assay medium. Pretreatment can render MPA more readily available to one or more of the assay reagents or more readily detectible by reducing interference in the assay by removing any unwanted materials. The sample may be pretreated to separate or lyse cells; precipitate, hydrolyse or denature proteins; hydrolyze lipids; solubilize the analyte; or the like. Such pretreatment may include, without limitation: centrifugation; treatment of the sample with an organic solvent, for example, an alcohol, preferably an alcohol having less than 7 carbon atoms such as methanol; and treatment with detergents.

The assay will normally be carried out in an aqueous buffered medium at a moderate pH, generally that which provides optimum assay sensitivity.

The aqueous medium may be solely water or may include from 0–40 volume percent of a cosolvent. The pH for the medium will usually be in the range of 4–11, more usually in the range of 5–10, and preferably in the range of 6.5–9.5. The pH will usually be a compromise between optimum binding of the binding members of any specific binding pairs and the pH optimum for other reagents of the assay such as members of the signal producing system.

Various buffers may be used to achieve the desired pH and maintain the pH during the determination. Illustrative buffers include borate, phosphate, carbonate, tris and barbital. The particular buffer employed is not critical to this invention, but in an individual assay one or another buffer may be preferred.

Moderate temperatures are normally employed for carrying out the assay and usually constant temperatures during the period of the measurement, particularly for rate determinations. Incubation temperatures will normally range from 5–45° C., more usually from 15–40° C. Temperatures during measurements will generally range from 10–50° C., more usually from 15–40° C.

The concentration of MPA which may be assayed will generally vary from $10^{-5}$ to $10^{-13}$ M, more usually from $10^{-6}$ to $10^{-8}$ M. Considerations, such as whether the assay is qualitative, semiquantitative or quantitative (relative to the amount of MPA present in the sample), the particular detection technique and the concentration of the MPA will normally determine the concentrations of the various reagents.

The concentrations of the various reagents in the assay medium will generally be determined by the concentration range of interest of MPA. However, the final concentration of each of the reagents will normally be determined empirically to optimize the sensitivity of the assay over the range. That is, a variation in concentration of MPA which is of significance should provide an accurately measurable signal difference.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially. Optionally, an incubation step may be involved subsequent to each addition, generally ranging from 30 seconds to 6 hours, more usually from 1 minute to 1 hour.

The following examples further describe the specific embodiments of the invention, and are intended to describe and not to limit the scope of the invention.

In a homogeneous assay after all of the reagents have been combined, the signal is determined and related to the amount of MPA in the sample tested. For example, in EMIT, a sample suspected of containing MPA is combined in an aqueous medium either simultaneously or sequentially with an MPA-enzyme conjugate and antibody capable of recognizing MPA and the conjugate. Generally, a substrate for the enzyme is added which results in the formation of a chromogenic or fluorogenic product upon enzyme catalyzed reaction. Preferred enzymes are glucose-6-phosphate dehydrogenase and alkaline phosphatase. The MPA in the sample and the MPA-enzyme conjugate compete for binding sites on the antibody. The enzyme activity in the medium is then determined, usually by spectrophotometric means, and is compared to the enzyme activity determined when calibrators or reference samples are tested in which a known amount of MPA is present. Typically, the calibrators are tested in a manner similar to the testing of the sample suspected of containing MPA. The calibrators will typically contain differing, but known, concentrations of the MPA analyte to be determined. Preferably, the concentration ranges present in the calibrators will span the range of suspected MPA concentrations in the unknown samples.

Heterogeneous assays usually involve one or more separation steps and can be competitive or non-competitive. A variety of competitive and non-competitive assay formats are disclosed in Davalian, et al., U.S. Pat. No. 5,089,390, column 14, line 25 to column 15, line 9, incorporated herein by reference. In a typical competitive assay an antibody of the invention is bound to a support, then contacted with a medium containing the sample and a MPA conjugated to a detectable label, such as an enzyme. MPA in the sample competes with the conjugate for binding to the antibody. After separating the support and the medium, the label activity of the support or the medium is determined by conventional techniques and related to the amount of MPA in the sample.

A typical non-competitive assay is a sandwich assay disclosed in David, et al., U.S. Pat. No. 4,486,530, column 8, line 6 to column 15, line 63, incorporated herein by reference. In this method, an immune sandwich complex is formed comprising MPA, a first antibody (monoclonal or polyclonal) that binds to MPA and a second antibody that binds to MPA. Subsequently, the immune sandwich complex is detected and is related to the amount of MPA in the sample. The immune sandwich complex is detected by virtue of the presence in the complex of a label wherein either or both the first antibody and the second antibody contain labels or substituents capable of combining with labels, such as, for example, linking the antibody to biotin and providing avidin bound to a label.

Another method useful for carrying out the present invention is disclosed in Weng, et al., U.S. Pat. No. 4,879,214, column 9, line 11, to column 12, line 39, incorporated herein by reference. The method involves providing in combination a test solution containing the sample, a first sbp member and a contact portion of a test strip of bibulous material capable of being traversed by the test solution by means of capillary action. The first sbp member can be capable of binding the analyte. The strip contains a second sbp member for concentrating and non-diffusively binding the first sbp member at a small situs on the strip separated from the contact portion of the strip. The strip can further contain a third sbp member between the small situs and the contact portion. A detectible signal is produced in relation to the presence of the analyte in the test solution.

Another method that is useful in carrying out the assay of this invention is disclosed in Ullman, et al., U.S. Pat. No. 4,857,453, column 11, line 21 to column 14, line 42, and column 18, line 21 to column 21, line 55, incorporated herein by reference.

Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

A preferred method of the invention for determining MPA in a sample suspected of containing MPA comprises the steps of: (a) contacting the sample with an antibody that binds MPA; and (b) detecting the binding of the antibody to MPA. The antibody is raised to one of the following immunogens:

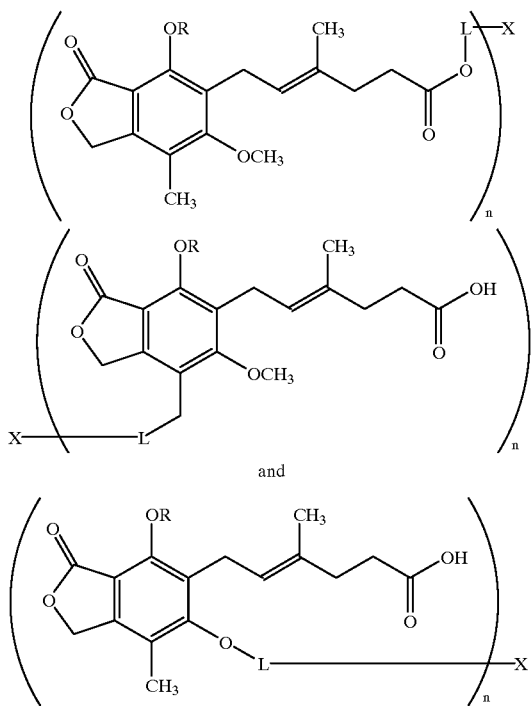

where X is an immunogenic carrier, L is a bond or a linking group, R is selected from the group consisting of H, lower alkyl, and CO-lower alkyl, and n is a number from 1 up to the molecular weight of X divided by 5000. The antibody can be bound to a support or capable of being bound to a support. In this method, step (a) can further comprise contacting the sample with one of the following compounds:

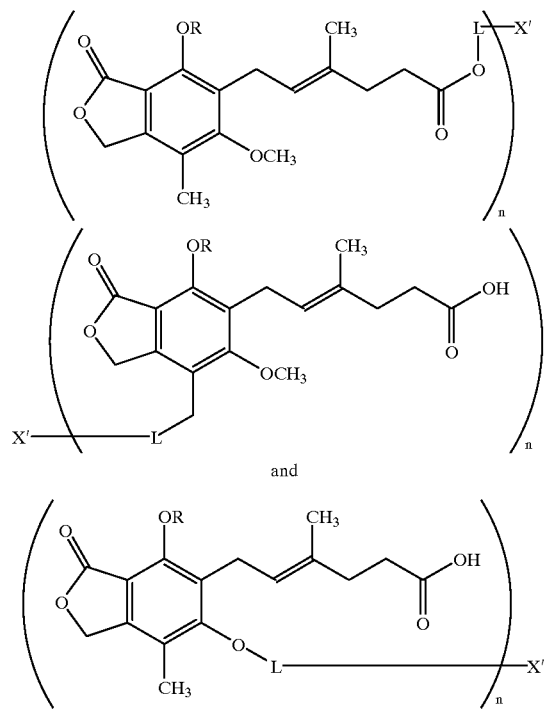

where X' is a detectable label, L is a bond or a linking group, R is selected from the group consisting of H, lower alkyl, and CO-lower alkyl, and n is a number from 1 up to the molecular weight of X' divided by 5000.

Another preferred method of the invention for measuring the amount of MPA in a sample suspected of containing MPA, comprises the steps of: (a) combining in an aqueous medium: the sample, MPA conjugated to a detectable label, and an antibody capable of distinguishing between MPA and a compound selected from the group consisting of mycophenolate esters and MPA metabolites; and (b) determining the effect of the sample on the activity of the label. The detectable label is preferably an enzyme and the determining step involves measuring the activity of the enzyme. The method can also include substrates for the enzyme in the combining step.

Another preferred method is a homogeneous immunoassay for MPA in a sample suspected of containing MPA which comprises: (a) combining in a liquid medium: the sample, a conjugate of an analog of MPA and an enzyme, an antibody capable of distinguishing between MPA and mycophenolate esters, and substrates for the enzyme; (b) determining the enzymatic activity of the enzyme in the medium; and (c) comparing the activity to the enzymatic activity observed with a sample containing a known amount of MPA.

The present invention also relates to compositions of matter comprising complexes formed from an antibody of the invention and MPA. Such complexes are useful as calibrators in the methods of the invention wherein the method is calibrated by determining the amount of MPA in a calibration solution having a known concentration of MPA. Thus, the present invention also relates to a method for preparing such a composition comprising the step of combining in a liquid medium: MPA and an antibody of the invention. Such complexes can be packaged in the kit aspects of the invention for use in such calibrations.

Another aspect of the present invention relates to kits useful for conveniently performing the assay methods of the invention for the determination of MPA. To enhance the versatility of the subject invention, reagents useful in the methods of the invention can be provided in packaged combination, in the same or separate containers, in liquid or lyophilized form so that the ratio of the reagents provides for substantial optimization of the method and assay. The reagents may each be in separate containers or various reagents can be combined in one or more containers depending on the cross-reactivity and stability of the reagents.

The kit contains an antibody of the invention raised in response to an analog of MPA conjugated, optionally through a linking group, to an immunogenic carrier. Suitable immunogens include:

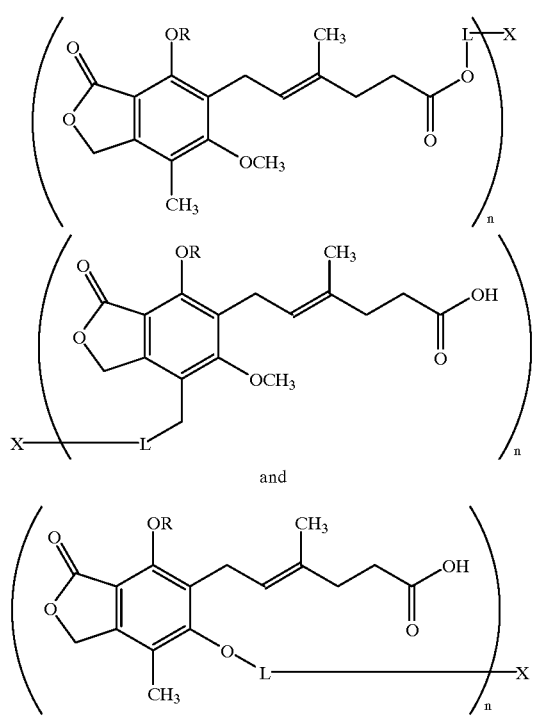

where X is an immunogenic carrier, L is a bond or a linking group, R is selected from the group consisting of H, lower alkyl, and CO-lower alkyl, and n is a number from 1 up to the molecular weight of X divided by 5000. Preferably, the antibody can distinguish between MPA and mycophenolate esters and/or MPA metabolites. Such antibodies can be labeled or unlabeled.

The kit can also comprise as a reagent MPA or an MPA analog conjugated, optionally through a linking group, to a label. Suitable conjugates include:

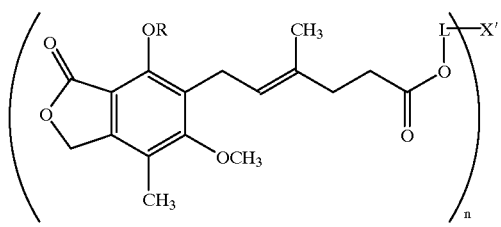

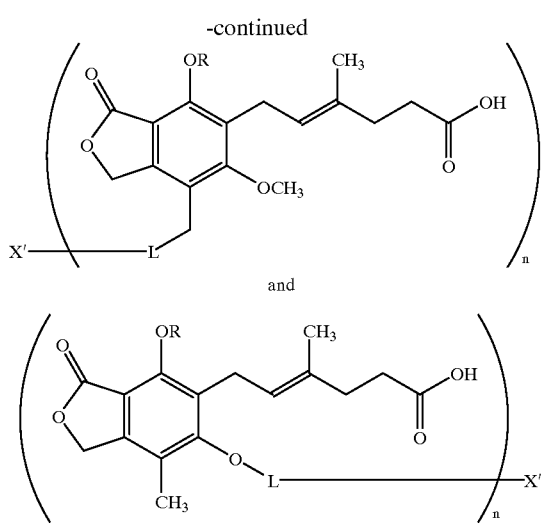

where X' is a detectable label, L is a bond or a linking group, R is selected from the group consisting of H, lower alkyl, and CO-lower alkyl, and n is a number from 1 up to the molecular weight of X' divided by 5000.

Another reagent useful for conducting the assay aspects of the invention is a complex formed from an antibody of the invention and a labeled MPA conjugate of the invention. Such kits can further comprise other packaged reagents for conducting assay aspects of the invention including, by way of example and not limitation, members of a signal producing system, supports, ancillary reagents, and so forth. In a preferred embodiment, the kit comprises in packaged combination: (a) an antibody capable of distinguishing between MPA and mycophenolate esters, and (b) a compound comprising MPA bound to a detectable label.

Preferably, the pH of a labeled MPA conjugate reagent is optimized to balance, among any other considerations, the activity and stability of the conjugate. In one of its preferred embodiments, this present invention relates to MPA-G6PDH or MPA-alkaline phosphatase conjugate reagents wherein the pH is 6–10, preferably 7–9, more preferably 7.5–8.5.

Preferably, the pH of antibody reagent is optimized to maximize the stability and precision of assay reagent components. In one of its preferred embodiments, the present invention relates to MPA antibody reagents wherein the pH is 4–7, preferably 5–6, more preferably 5.25–5.85.

Surface active additives, including bulking agents such as BLG or PEG; defoamers and surfactants such as Tween-20, Plurafax A38, Triton X-100, Pluronic 25R2, RSA, bovine serum albumin, Mod-u-cyte, sol-u-pro, or the like; and other materials commonly used in the art can be added to both antibody and label conjugate reagents. Surface active additives can be added in order to maintain hydrophobic or compounds of low solubility in solution, stabilize assay reagent components, or optimize assay reagent activity. Anti-microbial agents can be added to assay reagents in order to extend the storage life of the reagents.

The invention is demonstrated further by the following illustrative examples.

EXAMPLES

Parts and percentages herein are by weight unless otherwise indicated. Temperatures are in degrees Centigrade (° C.). Column chromatography separations were performed on silica gel (Merck, 230–400 mesh). All the reactions were conducted under an atmosphere of dried argon. The reagents used are all commercially available.

| Abbreviations | |
|---|---|
| ALP | Alkaline phosphatase |
| BSA | Bovine Serum Albumin |
| DMEM | Dulbecco's Modified Eagle Medium |
| DMF | N,N-Dimethylformamide |
| ELISA | Enzyme Linked Immunosorbent Assay |
| EMIT | Enzyme Multiplied Immunoassay Technique |
| FA | Freund's Adjuvant |
| G6PDH | Glucose-6-Phosphate Dehydrogenase |
| KLH | Keyhole limpet hemocyanin |
| MPA | mycophenolic acid |
| MPA-M | morpholinoethyl E-6-(1,3-dihydro-4-hydroxy-6-methoxy-7-methyl-3-oxo-5-isobenzofuranyl)-4-methyl-4-hexenoate |
| MPA-G | mycophenolic acid glucuronide |
| NHS | N-hydroxysuccinamide |
| OD | Optical Density |
| PBS | Phosphate Buffered Saline |
| SAT | Serum Antibody Titer |

Example 1

Oxidation of MPA to Hydroxymethyl-MPA

A stirred solution of MPA (5 g, 34.5 mmol) and NaOH (7 g) in water (100 mL) was warmed to 70–80° C. for 1 hour under an argon atmosphere. The mixture was then cooled to 0° C., and a solution of potassium ferricyanide (4 g, 21.3 mmol) in water (100 mL) was added over a period of 30 min. After 4 hours, more potassium ferricyanide (2 g, 10.6 mmol) in water (50 mL) was added. The reaction was then stirred overnight at room temperature. The mixture was then acidified with HCl (3N) to pH 2.0 and then the mixture was extracted with ethyl acetate (2×150 mL). The organic extract was then washed with water:brine (1:1, 100 mL) and dried ($MgSO_4$). The solvent was removed under reduced pressure to give the crude product which was purified by column chromatography (ethyl acetate:hexane: acetic acid, 60:40:1) to give the pure hydroxymethyl-MPA product as a white solid (2.0 g, 40%).

Example 2

Preparation of Chloromethyl-MPA from Hydroxymethyl-MPA

A suspension of hydroxymethyl-MPA (400 mg, 1.2 mmol) in acetyl chloride (10 mL) was stirred at room temperature for 3 hours until it became a clear solution. The excess acetyl chloride was removed under the reduced pressure, and the residue was dissolved in ethyl acetate (40 mL) and was washed with water (3×50 mL) or until the aqueous wash was neutral. The organic phase was then dried ($MgSO_4$) and evaporated to dryness to give chloromethyl-MPA (300 mg, 63%) as a thick liquid, which was used for the next step without further purification.

Example 3

Preparation of Dithiol Extended MPA

To a stirred solution of chloromethyl-MPA (200 mg, 0.5 mmol) in acetone (5 mL) was added 1,2-ethanedithiol (0.25 mL, 3 mmol) and potassium carbonate (200 mg, fine powder). The reaction was stirred for 3 hours and then was filtered. The filter cake was washed with acetone (10 mL) and the filtrate was then evaporated to dryness. Ethyl acetate (50 mL) was added, and the mixture was washed with water (3×100 mL) and dried ($MgSO_4$). The solvent was removed under reduced pressure, and the residue was subjected to silica gel column chromatography (ethyl acetate:hexane:acetic acid, 60:40:0.1) to give MPA-7-(2-thiomethyl-ethanethiol) ("dithiol extended MPA") as a thick oil (150 mg, 72%):

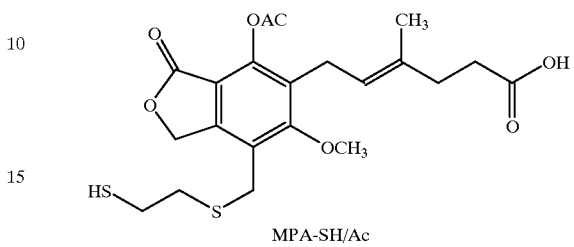

MPA-SH/Ac

Example 4

Conjugation of Dithiol Extended MPA to Bromoacetyl-KLH

To a stirred solution of bromoacetyl-KLH (26 mg, 1.3 mg/mL, $5\times10^{-5}$ mmol, number of acetyl groups ≅1100 in phosphate buffer (pH≅8.5, 100 mM) was added DMF (2 mL). A solution of dithiol extended MPA (20 mg, $4.8\times10^{-2}$ mmol) in DMF (1 mL) was added under an argon atmosphere.

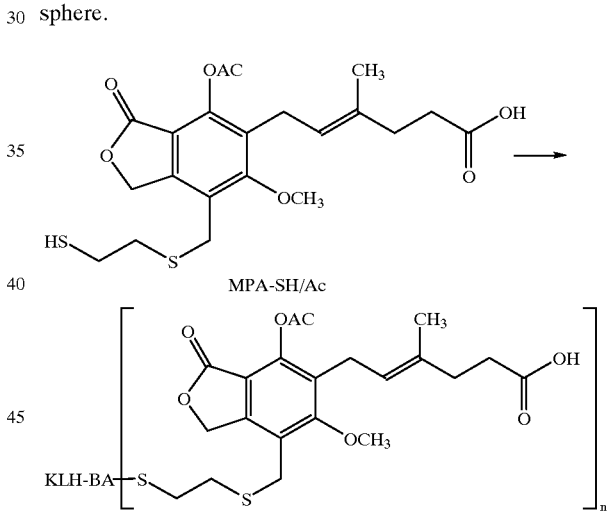

The reaction mixture was then stirred for 24 hours under argon atmosphere at room temperature. The resulting solution was then passed through a Sephadex G-50 column (phosphate buffer, pH=8.0, 100 mM was used as eluant) to give the solution of the dithiol extended MPA-bromoacetyl-KLH immunogen (40 mL, 0.5 mg/mL). The hapten number was determined to be 500, according to the method described in Habeeb, *Analytical Biochemistry* 14:328–336 (1966).

Example 5

Conjugation of MPA to KLH

To a stirred solution of MPA (32 mg, 0.1 mmol) in acetonitrile (1 mL) and pyridine (160 mg) was added disuccinyl carbonate as a solid, portionwise (≅10 mg per portion) and the reaction was monitored by TLC (silica gel, ethyl acetate:hexane:acetic acid, 50:50:1) until no starting material was left (≅4 hours). The resulting MPA-NHS ester mixture was used for the next step without further purification. To a stirred solution of KLH (40 mg, 8×10$^{-6}$ mmol) in deionized water (5 mL) and acetonitrile (0.5 mL) was added a NaOH solution (1N) until the pH was 9.0. To the resulting solution at 4° C. was added a solution of MPA-NHS ester (270 μL, ≅0.03 mmol). The mixture was stirred overnight at 4° C. and then was purified by dialyzing against a mixture of water and DMF (80:20) and then water and DMF (90:10) and finally water. The resulting solution was freeze dried to give the pure MPA-KLH immunogen (50 mg), with KLH bound at the 1' position of the MPA isobenzofuranyl ring system. The hapten number was determined to be 1200.

Example 6

Conjugation of MPA to G6PDH

Using the method of Example 5, a series of 4 enzyme-conjugates were prepared differing in how heavily the enzyme was deactivated, i.e., the more deactivated the enzyme, the larger the number of haptens were labeled to the enzyme. MPA-G6PDH-conjugate A was deactivated by 23%, B by 38%, C by 52%, and D by 71%.

Example 7

Conjugation of Dithiol Extended MPA to G6PDH

Using the method of Example 4, a series of enzyme-conjugates was prepared using the dithiol extended MPA hapten. Dithiol extended MPA-G6PDH conjugate A was deactivated by 35%, B by 48%, C by 52%, and D by 77%.

Example 8

Production of Antibodies

Methods

A. Immunizations

Mice were immunized with the immunogen of Example 4 and/or 5 in one of the following adjuvants: Complete and Incomplete FA, Alum, and RIBI Adjuvant System, consisting of trehalose dimycolate and monophosphoryl lipid A. Immunogens were administered at 20 to 122 μg per intraperitoneal injection, monthly, 2 to 4 times. Three days prior to the fusion, mice received a saline intraperitoneal boost containing 200 to 500 μg/mL of immunogen.

B. Tissue Culture

Super DMEM was used for all tissue culture. It consisted of DMEM supplemented with: 10% fetal bovine serum, 10% NCTC-135 (Gibco #440–1100EC), 4 mM glutamine, 1 mM oxaloacetic acid, 1 mM sodium pyruvate, 0.148 nM 1-cysteine, 10 μg/mL insulin, and 35.5 mM sodium bicarbonate.

Conditioned media was prepared by growing P388D$_1$ cells (ATCC #TIB 63) in Super DMEM and splitting 1:4 every four to five days. Spent media was centrifuged at 1500 rpm for 15 minutes. The spent media was then filtered to remove any remaining cells and debris. Glutamine (100× stock=58.5 g/L) was added to the spent media before using or freezing at −20° C. for future use. Conditioned Super DMEM was prepared by supplementing Super DMEM with 10% P388D$_1$ spent media and then using it to support hybridoma growth after fusion and during cloning.

Mouse myeloma cell line P3/X63-Ag 8.653 (Ag8.653) was maintained in culture by splitting 1:2 to 1:4 daily or by serial dilution in a 6-well plate for the weekend. All cells were maintained at 37° C. in 7% CO$_2$.

1. Fusion

The spleen was aseptically removed from an immunized mouse, placed in 10 mL DMEM, minced, then mashed between two slides. A single cell suspension of splenocytes was attained by passing the cell suspension through a monofilament screen cloth. The splenocytes from two spleens, about 2×10$^8$ cells, were combined with 40×10$^6$ Ag8.653 cells, centrifuged at 800 rpm for 5 minutes, and washed 1 to 2 times with DMEM. Fusions were performed by addition of 4.0 mL PEG (50% solution in 75 mM Hepes), which was added over 3 minutes while gently stirring, and then 30 to 40 mL Super DMEM was added to inactivate the PEG. The cell suspension was centrifuged at 800 rpm for 5 minutes. Supernatant was poured off, and the cells were resuspended with 240 mL Super DMEM-HAT (stock HAT= 50X Sigma #H0262; in media: 100 μM hypoxanthine, 0.4 μM aminopterin, and 16 μM thymidine) and plated at 200 μL/well into twelve 96-well culture plates.

Cells were fed by removal of 100 μL/well of spent media and subsequent addition of 200 μL/well of conditioned Super DMEM-HAT 4 to 5 days after the fusion.

Fusions were screened about 7 to 10 days after the fusion. Cells were ultimately cloned by serial dilution as described below.

2. Cloning by Serial Dilution

Wells which were positive by ELISA were then tested in the EMIT format. Hybridomas producing ELISA and EMIT positive antibodies were then cloned several times by serial dilution to ensure single cell colonies.

Hybridomas from a well of a 96-well plate were transferred to a well in a 24-well plate containing 1.5 mL/well of conditioned Super DMEM. Cells were mixed by pipetting, and 100 μL/well were added to row A of a 96-well plate containing 200 μL/well conditioned Super DMEM. One hundred μL/well were transferred to row B using a Flow Multichannel pipettor, mixed by pipetting, and again transferring 100 μL/well to the next row. Each "clone" was serially diluted 7 times, one to 4 clones per plate. Cells were recloned by limiting dilution 3 to 4 times or until stable.

3. Freezing and Thawing Cell Lines

Cloned and stabilized cell lines prepared using the immunogens of Examples 4 and 5 that were ELISA positive and cell lines that inhibited the enzyme-conjugate and modulated with free drug in the EMIT protocol from subsequent fusions were frozen and stored at −100° C. The chosen well (clone) from a 96-well plate was grown up by daily passaging of cells and sequentially expanding from a 24-well plate with 1.5 mL/well Super DMEM, next into a 6-well plate with 8 mL/well Super DMEM, and finally into a T-75 flask with 50 mL Super DMEM.

Cells from the T-75 flask (about 15×10$^6$ cells/flask) were centrifuged at 800 rpm for 5 minutes and resuspended in 3 mL of freezing medium, 10% dimethylsulfoxide and an additional 10% fetal bovine serum in Super DMEM. One-mL aliquots were pipetted into vials and stored at −100° C.

Cells were thawed by warming the vials in a 37° C. water bath. The cell suspension was centrifuged with 5 mL of Super DMEM at 800 rpm for 5 minutes. The supernatant was decanted and the cells resuspended in 8 mL of Super DMEM and pipetted into a 6-well plate for cell expansion.

C. Screening

All ELISA screens were performed at room temperature.

1. ELISA Reagents

PBS, pH 7.2: 0.01 M sodium phosphate, 0.15 M NaCl, and 0.002% sodium azide.

ELISA Wash Buffer: 0.5% Tween 20 in PBS.

Plate Coat: rabbit anti-mouse IgG+A+M(H+L), reconstituted with 2 mL water per manufacturers directions, and diluted 1:100 in PBS.

Plate block: 1% BSA in PBS.

Diluent: 0.5% BSA in PBS; diluted plate block 1:2 in PBS.

ELISA dithiol extended MPA-G6PDH conjugate, in accordance with Example 7: diluted 1:500 in 0.5% BSA/PBS.

Substrate: 0.053 M Trizma Base (Sigma), 0.02 M NAD, 0.033 M glucose-6-phosphate, 0.025% sodium azide, 0.6 mM p-iodonitrotetrazilium violet (Sigma), 1 µg/mL BSA, 0.6 units/mL diaphorase (Sigma #2381), pH adjusted to 6.2 with HCl.

2. Reverse ELISA Protocol

This protocol was used for primary and cloning plate screens. The plates were coated with rabbit anti-mouse, 50 µL/well, and incubated. The wells were emptied then blocked with 300 µL/well, incubated and emptied again. Antibody (spent media, 50 µL/well) was added, incubated, then washed. Dithiol extended MPA-G6PDH conjugate (50 µL/well) from Example 7 was added, incubated, then washed. Substrate (100 µL/well) was added and incubated. OD greater than about 0.5 were considered ELISA positive.

3. Competitive Reverse ELISA Protocol

This assay was used to determine the antibody's ability to bind to free MPA preferentially in the presence of MPA-enzyme conjugate. A panel of antibodies were tested against decreasing concentrations of free MPA in MPA-enzyme conjugate solutions. The assay protocol was the same as that for the reverse ELISA, except where 50 µL/well of dithiol extended MPA-G6PDH conjugate was added. Instead, MPA, diluted in the dithiol extended MPA-G6PDH conjugate solution, was added 50 µL/well, in the following concentrations of µg MPA per mL conjugate solution: 100 µg/mL, 1 µg/mL, 10 ng/mL, 100 pg/mL, and 1 pg/mL. This was then incubated and washed as described above. Percent competition was computed as:

$$\% \ \text{Competition} = \frac{\text{OD w/E-C only} - \text{OD w/drug}}{\text{OD w/E-C only}}$$

where the term "E-C" is the dithiol extended MPA-G6PDH conjugate.

4. Forward ELISA Reagents

The plate was coated with the dithiol extended MPA-G6PDH conjugate of Example 7, diluted 1:100 in PBS. Goat anti-mouse (IgG+IgM-ALP, diluted 1:500 in PBS) and subclass specific ALP-labeled antibodies, diluted 1:100 in PBS, were added.

5. Forward ELISA Protocol

This protocol was used to determine serum antibody titers ("SAT") of mice to monitor the relative effect of different immunizations, dose and type of immunogen, and adjuvant. Subclass of antibodies was also determined using a variation of this protocol.

Plates were coated with the dithiol extended MPA-G6PDH conjugate of Example 7 (50 µL/well), incubated and the wells emptied. The plates were blocked (300 µl/well), incubated and the contents emptied.

Antibody addition step—Antibody (50 µl/well) was added, incubated, then the plates washed. For SAT: Each serum sample was diluted 1:100 in BSA/PBS diluent in a test tube, then 300 µL was transferred to a well in column 1 of a preblocked microtiter plate containing 0.15 mL of BSA/PBS diluent in all wells between columns 2 to 12. Each serum sample was then diluted 1:2 serially, across the plate. Fifty µL/well were transferred from the dilution plate to the assay plate. For Subclass determination: Fifty µL/well of each antibody (spent media) was added across the plate, one antibody per row.

The dithiol extended MPA-G6PDH conjugate (50 µL/well) was added, incubated, then washed. For SAT: goat anti-mouse-ALP (50 µL/well) was added, incubated, then washed. For Subclass determination: Subclass specific ALP-labeled antibodies (50 µL/well) were added, with a different subclass antibody in every column.

Substrate (100 µL/well) was added, incubated, then read at 405 nm. For SAT: Dilution of serum at which there was 70% reduction of OD from the highest OD in the dilution curve. For Subclass determination: For each antibody, there were 3 positive wells: the control well (anti-mouse), heavy chain (one IgG subclass, IgM, or IgA), and one light chain.

6. EMIT Screening

Products from fusions using the immunogens of Examples 4 and 5 were screened by reverse ELISA. All positive hybridomas were cloned out before any EMIT testing occurred. The following fusions were screened by ELISA first, and the positive wells were then rescreened by EMIT.

EMIT assays were performed using Reagent A diluent (substrate), Reagent B (enzyme-conjugate) at $R_{max}$=250 ΔA/min, MPA calibrators in assay buffer, MPA-G in assay buffer, and MPA-M in DMF. Two protocols were used, one having a short incubation time and one having a long incubation time. The only difference between the short and long protocol was that the delay time (incubation of substrate+antibody+enzyme-conjugate) was increased in the long protocol from 25 to 175 seconds before the reaction was read. Assay buffer, Reagent A, and Reagent B diluents used were typical liquid EMIT®2000 formulations.

Primary screens were performed using a 3-reagent program. The MPA spent media antibodies were placed in the sample cups. The reagent rack contained Reagent A diluent in position A, Reagent B in position 1, and assay buffer, MPA calibrator, MPA-G, or MPA-M solutions in position 2. At least two tests were performed on each antibody: first spent media antibodies were tested for inhibition of the enzyme-conjugate, the %I, and then for modulation with free MPA or for cross-reactivity to MPA-G or MPA-M.

D. Production of In Vitro Antibody

All ELISA positive antibodies produced using the immunogens of Example 4 or 5 and antibodies from subsequent fusions which inhibited and modulated well in EMIT were expanded in culture. Hybridomas were overgrown to one-T75 flash (50 mL of spent media), two-T225 flasks (500 mL of spent media), and some eventually to four-T225 flasks (1L of spent media). Cells and debris were separated by centrifugation and filtration. Sodium azide was added at 0.2% before purification.

E. Purification of Antibody

Spent media antibodies of more interest, expanded to 500 mL or 1-L, were purified by Protein G column chromatography, at room temperature.

1. Reagents for Protein G Purification

Washing/binding buffer, PBS pH 7.0: 0.01 M sodium phosphate, 0.15 M sodium chloride, and 0.002% sodium azide.

Elution buffer: 0.5 M acetic acid adjusted to pH 3.0 with ammonium hydroxide.

Neutralizing solution: 1 M tris base.

Cleaning buffer: 1 M acetic acid (57.2 mL glacial acetic acid/1L).

2. Protein G purification protocol

A column was packed with 10 mL of Protein G-Sepharose and washed with washing/binding buffer. Antibody (spent media, 0.5 to 1L), was loaded onto the column. The column was washed with washing/binding buffer until OD returned to baseline. Antibody was eluted with elution buffer. Fifty drop (about 2.5 mL) fractions were collected into test tubes already containing 1.15 mL of neutralizing solution. The antibody peak was pooled and dialyzed overnight against 4 L PBS, pH 7.4. The column was washed with cleaning buffer and re-equilibrated with the washing/binding buffer, then stored in 4° C. Antibody purity was checked by Paragon electrophoreses for presence of a single band. Antibody concentration was determined by first getting an OD of the antibody solution at 280 nm, then calculating the concentration using the extinction coefficient for IgG: $A_{280}$ (1 mg/mL)=1.35 or IgM: $A_{280}$(1 mg/mL)=1.2.

Results

A. Serum Antibody Titers and ELISA Screening

To mount an immune response, first a group of mice were immunized with the immunogen of Example 5. Immunogen at different doses and in different adjuvants was used: 100 μg in FA, 20 μg in FA, and 20 μg in Alum. After 3 immunizations, mouse sera was tested for antibody titer with the dithiol extended MPA-G6PDH conjugate made in Example 7. Serum antibody titers of mice that received 100 μg in FA were slightly higher than the others, 1:100,000 to 1:200,000, while the serum antibody titers of mice that received 20 μg in Alum were the lowest, 1:50,000.

At a later time, a new group of mice were immunized with the dithiol extended MPA-bromoacetyl-KLH immunogen of Example 4. Some mice received 22 μg immunogen in Alum and some received 50 μg in FA. After 3 immunizations, serum antibody titers of both groups were comparable, 1:8000.

Sera from the group of mice that received the immunogen of Example 4, produced a much stronger signal in the ELISA, 2 to 2.5 OD units, and steeper titration curves, while the sera from the group of mice that received the immunogen of Example 5, produced a weak signal, 0.5 to 1.2 OD units, and flat titration curves. These differences are probably due to the enzyme-conjugate used. The MPA linkages in both reagents, the second immunogen and the enzyme-conjugate used in the ELISA, were identical. Binding between the antibodies produced using the immunogen of Example 4 and the enzyme-conjugate of Example 7 is stronger than with the antibodies produced against the unmatched, carboxyl-linked KLH immunogen of Example 5.

Products of fusions using the immunogen of Example 4 or 5 were performed before any assay development work started. Fusions were screened by the reverse ELISA screen only. All ELISA positive hybridomas were cloned and stabilized. They were later used for assay development.

Once the hybridomas produced using the immunogen of Example 4 or 5 were stabilized, spent media antibodies were tested in a competitive reverse ELISA to determine relative affinities of these antibodies. In this assay, immobilized antibodies were incubated with varying amounts of free MPA in the presence of an optimized level of enzyme-conjugate. The antibody's preferential binding to free MPA vs. enzyme-conjugate is calculated as % competition at every level of free MPA. Those antibodies which bind to free MPA (i.e., compete with enzyme-conjugate) at the lower concentrations of the free MPA are considered to be of higher affinity than those antibodies that compete only with higher levels of free drug. Tables 1A and 1B summarize the competitive ELISA data of antibodies.

TABLE 1A

Summary of data for antibodies (immunogen of Example 5) tested by the Competitive Reverse ELISA at different concentrations of MPA.

| Clone | MPA 10 ng/mL in E-C | | MPA 100 pg/mL in E-C | | MPA 1 pg/mL in E-C | |
| --- | --- | --- | --- | --- | --- | --- |
| | Avg OD | % Comp | Avg OD | % Comp | Avg OD | % Comp |
| 1B8 | 0.542 | 43 | 1.021 | | 1.097 | |
| 1F9 | 0.356 | 61 | 0.795 | 12 | 0.991 | |
| 3B4 | 0.496 | 63 | 1.147 | 14 | 1.319 | |
| 5G4 | 0.646 | 57 | 1.373 | 9 | 1.540 | |
| 6F1 | 0.269 | 80 | 1.033 | 24 | 1.328 | |
| 7E9 | 0.299 | 77 | 1.043 | 19 | 1.297 | |
| 8A3 | 0.955 | 33 | 1.362 | 5 | 1.511 | |
| 8H1 | 0.411 | 67 | 0.930 | 26 | 1.271 | |
| 1B7 | 0.493 | 57 | 1.067 | 7 | 1.094 | 5 |
| 3A3 | 0.133 | 69 | 0.363 | 15 | 0.403 | 6 |
| 3D8 | 0.294 | 65 | 0.824 | | 0.844 | |
| 4G5 | 0.347 | 69 | 0.988 | 13 | 1.056 | 7 |
| 5A8 | 0.295 | 72 | 0.897 | 16 | 0.978 | 8 |
| 5G9 | 0.446 | 64 | 1.126 | 10 | 1.221 | |
| 5G11 | 0.104 | 88 | 0.720 | 15 | 1.016 | |
| 7B6 | 0.491 | 59 | 1.215 | | 1.282 | |
| 11A1 | 0.447 | 69 | 1.498 | | 1.651 | |
| 11H1 | 0.380 | 68 | 1.168 | | 1.269 | |
| 11H11 | 0.372 | 69 | 1.215 | | 1.299 | |

TABLE 1B

Summary of data for antibodies (immunogen of Example 4) tested by the Competitive Reverse ELISA at different concentrations of MPA.

| Clone | MPA 1.0 μg/mL in E-C | | MPA 10 ng/mL in E-C | |
| --- | --- | --- | --- | --- |
| | Avg OD | % Comp | Avg OD | % Comp |
| 1A7 | 0.159 | 87 | 0.974 | 20 |
| 1B5 | 1.067 | 6 | 1.142 | |
| 1F2 | 1.170 | 16 | 1.333 | |
| 1H3 | 0.428 | 68 | 0.626 | 53 |
| 2E3 | 0.090 | 84 | 0.344 | 38 |
| 2H12 | 0.248 | 83 | 1.277 | 14 |
| 4B9 | 0.279 | 58 | 0.579 | 13 |
| 4C7 | 0.554 | 40 | 0.882 | 5 |
| 5C7 | 0.054 | 85 | 0.134 | 62 |
| 5G1 | 0.329 | 57 | 0.696 | 9 |
| 6A8 | 0.949 | 5 | 1.014 | |
| 6B10 | 0.481 | 49 | 0.906 | |
| 6B3 | 1.097 | 17 | 1.225 | 7 |
| 6E2 | 0.629 | 52 | 1.249 | |
| 7C3 | 0.088 | 93 | 0.720 | 46 |
| 7G4 | 0.185 | 87 | 1.003 | 28 |
| 7H12 | 0.597 | 26 | 0.792 | |
| 8B7 | 1.392 | | 1.516 | |
| 8C7 | 0.733 | 48 | 1.313 | 7 |
| 9A12 | 1.307 | 14 | 1.471 | |
| 11A8 | 1.069 | 18 | 1.227 | 6 |
| 11G10 | 0.459 | 47 | 0.773 | 11 |
| 12D5 | 0.083 | 84 | 0.350 | 33 |
| 12G4 | 0.390 | 56 | 0.767 | 14 |

B. Early EMIT Screening

Antibodies were also tested on a COBAS MIRA, first in a short incubation time protocol. Using the ELISA enzyme-conjugate, not optimized for EMIT, 19 spent media antibodies were tested for inhibition of enzyme-conjugate. 95 μL of spent media antibody were added to a 325 μL test. One antibody inhibited the enzyme-conjugate by 11%. These antibodies were retested in the long incubation time protocol and 4 antibodies slightly inhibited the enzyme-conjugate by 10 to 14%. When tested with free drug, 2 of the 4 antibodies modulated most of the signal with 100 μg/mL of MPA. All EMIT testing from this point on utilized the long protocol.

C. Assay Feasibility Assessment

Thirty-two of the above spent media antibodies were tested in a simulated commercial EMIT Assay. Five antibodies were chosen for standard curve size and good cross-reactivity profile. The CV of one antibody was particularly high when tested for within run precision.

TABLE 2

Summary of EMIT data for antibodies with large EMIT standard curves. The enzyme conjugate of Example 6 was used.

| | MPA immunogen of Ex. 5 | | | | | | | MPA immunogen of Ex. 4 | | | |
|---|---|---|---|---|---|---|---|---|---|---|---|
| Antibody | 4G5 | 1B7 | 1F9 | 4D4 | 6F1 | 3D8 | 11H11 | 1H3 | 2G12 | 3H4 | 7C3 |
| Loading μL/T | 4 | 5 | 10 | 5 | 5 | 5 | 5 | 5 | 5 | 5 | 5 |
| MPA, μg/mL, Rates | | | | | | | | | | | |
| Rmax | 251.4 | 259.3 | 258.3 | 258.3 | 258.3 | 258.3 | 258.3 | 258.3 | 258.3 | 258.3 | 258.3 |
| N | 149.2 | 139.2 | 138.8 | 161.4 | 161.1 | 130.4 | 149.7 | 160.5 | 146.4 | 123.3 | 141.4 |
| 0.5 | 155.7 | 155.5 | 164.7 | 188.6 | 181.9 | 155.4 | 167.7 | 227.1 | 163.9 | 151.1 | 154.9 |
| 1.0 | 159.5 | 167.7 | 209.7 | 202.9 | 191.9 | 182.8 | 175.8 | 238.2 | 176.7 | 183.5 | 171.0 |
| 2.5 | 168.2 | 169.8 | 240.0 | 220.5 | 198.1 | 209.3 | 183.8 | 240.7 | 187.9 | 216.7 | 182.1 |
| 5.0 | 177.4 | 181.2 | 254.5 | 236.4 | 209.2 | 253.7 | 196.4 | 248.8 | 209.2 | 233.3 | 207.4 |
| 7.5 | 192.3 | 188.5 | 259.4 | 244.1 | 218.5 | 243.3 | 203.5 | 252.2 | 220.2 | 244.1 | 218.7 |
| 10.0 | 198.5 | 181.3 | 251.2 | 239.6 | 209.2 | 237.4 | 199.7 | 243.2 | 217.0 | 237.5 | 218.6 |
| MPA, μg/mL, Separations | | | | | | | | | | | |
| Neg-0.5 | 6.5 | 16.3 | 25.9 | 27.2 | 20.8 | 25.0 | 18.0 | 66.6 | 17.5 | 27.8 | 13.5 |
| 0.5–1.0 | 3.8 | 12.2 | 45.0 | 14.3 | 10.0 | 27.4 | 7.3 | 11.1 | 12.8 | 32.4 | 16.1 |
| 1.0–2.5 | 8.7 | 2.1 | 30.3 | 17.6 | 6.2 | 26.5 | 8.8 | 2.5 | 13.2 | 33.2 | 11.1 |
| 2.5–5.0 | 9.2 | 11.4 | 14.5 | 15.9 | 11.1 | 26.4 | 12.6 | 8.1 | 19.3 | 16.6 | 25.3 |
| 5.0–7.5 | 14.9 | 7.3 | 4.9 | 7.7 | 9.3 | 7.6 | 7.1 | 3.4 | 11.0 | 10.8 | 11.3 |
| 7.5–10. | 6.2 | −7.2 | −8.2 | −4.5 | −9.3 | −5.9 | −3.8 | −9.0 | −3.2 | −6.6 | −0.1 |
| Neg-10.0 | 49.3 | 42.1 | 112.4 | 78.2 | 48.1 | 107.0 | 50.0 | 82.7 | 70.6 | 114.2 | 77.2 |
| Cross-reactivity to MPA-M - quanitation of 50 μg/mL MPA-M as MPA, μg/mL (**) | | | | | | | | | | | |
| 50 μg/mL | 5.0 | 13.2 | 2.4 | 9.0 | 18.5 | 9.1 | 20.8 | 3.5 | 7.8 | 3.5 | 8.5 |
| % Cx | 10 | 26 | 5 | 18 | 37 | 18 | 42 | 7 | 16 | 7 | 17 |
| Cross-reactivity to MPA-G - quanitation of 50 μg/mL MPA-G as MPA, μg/mL (*) (**) | | | | | | | | | | | |
| % Cx | 0 | 2 | 1 | 2 | 5 | 1 | 6 | 13 | 1 | 1 | 1 |

(*) 10 μL spent media Ab/Test (loading not optimized).
(**) Cross-reactivity is determined by first running a sample containing the cross-reactant, i.e. 50 μg/mL of MPA-M. The rate was then used to obtain a concentration relative to MPA standard curve, then expressed as the apparent MPA concentration divided by the actual concentration of cross-reactant × 100.

| | MPA immunogen of Ex. 4 | MPA immunogen of Ex. 4 | | | | | MPA immunogen of Ex. 4 and 5 | | | |
|---|---|---|---|---|---|---|---|---|---|---|
| Antibody | 3H9 | 8C7 | 5D11 | 9C10 | 10D11 | 11F10 | 7H8 | 8C7 | 9B2 | 12C7 |
| Loading μL/T | 20 | 10 | 15 | 7.5 | 15 | 50 | 25 | 50 | 25 | 25 |
| MPA, μg/mL, Rates | | | | | | | | | | |
| Rmax | 251.4 | 251.4 | 259.3 | 259.3 | 259.3 | 259.3 | 251.8 | 251.8 | 251.8 | 251.8 |
| N | 167.4 | 176.1 | 188.3 | 186.3 | 163.8 | 182.3 | 158.3 | 159.1 | 170.8 | 163.9 |
| 0.5 | 176.0 | 187.7 | 193.7 | 192.9 | 169.3 | 190.5 | 170.1 | 175.9 | 186.7 | 181.9 |
| 1.0 | 185.0 | 195.2 | 198.9 | 197.4 | 173.0 | 191.0 | 181.0 | 188.2 | 198.2 | 190.3 |
| 2.5 | 195.1 | 201.1 | 205.4 | 209.4 | 182.1 | 203.6 | 191.7 | 207.8 | 208.7 | 202.4 |
| 5.0 | 209.1 | 211.1 | 219.4 | 226.2 | 195.7 | 218.1 | 210.4 | 217.3 | 225.3 | 214.3 |
| 7.5 | 215.8 | 222.4 | 228.0 | 235.0 | 203.5 | 227.6 | 217.9 | 228.1 | 231.2 | 224.6 |
| 10.0 | 222.1 | 226.5 | 231. | 237.2 | 208.8 | 231.2 | 216.6 | 225.4 | 232.2 | 223.4 |
| MPA, μg/mL, Separations | | | | | | | | | | |
| Neg-0.5 | 8.5 | 11.6 | 5.4 | 6.6 | 5.5 | 8.2 | 11.8 | 16.8 | 15.9 | 18.0 |
| 0.5–1.0 | 9.1 | 7.5 | 5.2 | 4.5 | 3.7 | 0.4 | 10.9 | 12.3 | 11.5 | 8.4 |
| 1.0–2.5 | 10.1 | 5.9 | 6.5 | 12.0 | 9.1 | 12.7 | 10.7 | 19.6 | 10.5 | 12.1 |
| 2.5–5.0 | 14.0 | 10.0 | 14.0 | 16.8 | 13.6 | 14.5 | 18.7 | 9.5 | 16.6 | 11.9 |

TABLE 2-continued

Summary of EMIT data for antibodies with large EMIT standard curves. The enzyme conjugate of Example 6 was used.

| 5.0–7.5 | 6.7 | 11.3 | 8.5 | 8.8 | 7.8 | 9.5 | 7.5 | 10.8 | 5.9 | 10.3 |
|---|---|---|---|---|---|---|---|---|---|---|
| 7.5–10. | 6.3 | 4.1 | 3.4 | 2.2 | 5.3 | 3.6 | −1.3 | −2.7 | 1.0 | −1.2 |
| Neg-10.0 | 54.7 | 50.4 | 43.0 | 50.9 | 45.0 | 48.9 | 58.3 | 66.3 | 61.4 | 59.5 |

Cross-reactivity to MPA-M - quantitation of 50 μg/mL MPA-M as MPA, μg/mL: (**)

| μg/mL | 0.1 | 0.6 | 0.0 | 0.0 | 9.9 | 1.1 | 9.9 | 14.1 | 9.5 | 9.3 |
|---|---|---|---|---|---|---|---|---|---|---|
| % Cx | 1 | 1 | 0 | 0.1 | 20 | 2 | 20 | 28 | 19 | 19 |

Cross-reactivity to MPA-G - quantitation of either 50 or 1000 μg/mL MPA-G as MPA, μg/mL: (**) % Cx

| with 50 μg/mL | 3 | 2 | | | | |
|---|---|---|---|---|---|---|
| with 1000 μg/mL | | | 1.8 | 2.8 | 2.7 | 6 |

(**) Cross-reactivity is determined by first running a sample containing the cross-reactant, i.e. 50 μg/mL of MPA-M. The rate was then used to obtain a concentration relative to MPA standard curve, then expressed as the apparent MPA concentration divided by the actual concentration of cross-reactant X 100.

Antibody, 3D8, made against the carboxyl-linked immunogen of Example 5 was selected as a preferred antibody. Although it cross-reacted with MPA-M (18% with DMF matrix vs. 144% with plasma matrix), it produced a large standard curve, 112 units, and had excellent CV's, 1.9 to 5.8%.

Example 10

Biotinylation of MPA Antibodies

Purified antibody was dialyzed against 200 mM sodium bicarbonate, 150 mM sodium chloride, pH 8.8, overnight at 4° C. with three changes of buffer. A 10 mg/mL solution of biotin-NHS ester was made in dry DMF.

The biotin-NHS was added to aliquots of antibody to give biotin-NHS/antibody molar ratios between 2 and 80. The mixture was vortexed for 2 minutes then allowed to sit at room temperature for 1 hour. The unbound biotin NHS was separated from the labeled antibody using a Sephadex G25-80 column with 200 mM sodium bicarbonate, 150 mM sodium chloride, pH 8.8, as the mobile phase.

These biotinylated antibodies would be useful in a heterogenous immunoassay where avidin was bound to a support.

While the present invention has been described with reference to the specific embodiments thereof, it will be understood by and obvious to those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for the determination of mycophenolic acid in a sample suspected of containing mycophenolic acid comprising the steps of:
   (a) contacting said sample with a monoclonal antibody capable of distinguishing between mycophenolic acid and mycophenolate esters; and
   (b) detecting the binding of said antibody to mycophenolic acid, the presence of said binding indicating the presence and/or the amount of mycophenolic acid in said sample.

2. The method of claim 1 wherein said ester is morpholinoethyl E-6-(1,3-dihydro-4-hydroxy-6-methoxy-7-methyl-3-oxo-5-isobenzofuranyl)-4-methyl-4-hexenoate.

3. The method of claim 1 wherein step (a) further comprises contacting said sample with a labeled analog of mycophenolic acid.

4. The method of claim 1 wherein said antibody is bound to a support or capable of being bound to a support.

5. A method for the determination of mycophenolic acid in a sample suspected of containing mycophenolic acid comprising the steps of:
   (a) contacting said sample with a monoclonal antibody capable of distinguishing between mycophenolic acid and a metabolite of mycophenolic acid; and
   (b) detecting the binding of said antibody to mycophenolic acid, the presence of said binding indicating the presence and/or the amount of mycophenolic acid in said sample.

6. The method of claim 5 wherein said metabolite is mycophenolic acid glucuronide.

7. The method of claim 5 wherein step (a) further comprises contacting said sample with a labeled analog of mycophenolic acid.

8. The method of claim 5 wherein said antibody is bound to a support or capable of being bound to a support.

9. A method for the determination of mycophenolic acid in a sample suspected of containing mycophenolic acid comprising the steps of:
   (a) contacting said sample with a monoclonal antibody that binds mycophenolic acid: and
   (b) detecting the binding of said antibody to mycophenolic acid; wherein said antibody is raised to an immunogen selected from the group consisting of:

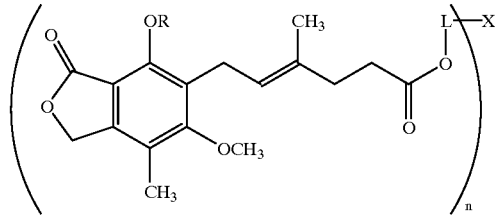

-continued

[structure with OR, CH3, OCH3, X-L, subscript n]

and

[structure with OR, CH3, CH3, O-L-X, subscript n]

wherein:
X is an immunogenic carrier,
L is a bond or a linking group,
R is selected from the group consisting of H, lower alkyl, and CO-lower alkyl, and
n is a number from 1 up to the molecular weight of X divided by 5000 and wherein the presence of said binding indicates the presence and/or the amount of mycophenolic acid in said sample.

10. The method of claim 9 wherein step (a) further comprises contacting said sample with a compound selected from the group consisting of:

[structure with OR, CH3, L-X', OCH3, CH3, subscript n]

[structure with OR, CH3, OH, OCH3, X'-L, subscript n]

and

[structure with OR, CH3, OH, CH3, O-L-X', subscript n]

wherein:
X' is a detectable label,
L is a bond or a linking group,
R is selected from the group consisting of H, lower alkyl, and CO-lower alkyl, and n is a number from 1 up to the molecular weight of X' divided by 5000.

11. The method of claim 9 wherein said antibody is bound to a support or capable of being bound to a support.

12. A method for measuring the amount of mycophenolic acid in a sample suspected of containing mycophenolic acid which comprises the steps of:
   (a) combining in an aqueous medium:
      (i) said sample
      (ii) mycophenolic acid conjugated to a detectable label, and
      (iii) a monoclonal antibody capable of distinguishing between mycophenolic acid and a compound selected from the group consisting of mycophenolate esters and MPA metabolites; and
   (b) determining the effect of said sample on the activity of said label wherein the activity of said sample is related to the presence and/or amount of mycophenolic acid in said sample.

13. The method of claim 12 wherein said compound is selected from the group consisting of morpholinoethyl E-6-(1,3-dihydro-4-hydroxy-6-methoxy-7-methyl-3-oxo-5-isobenzofuranyl)-4-methyl-4-hexenoate and mycophenolic acid glucuronide.

14. The method of claim 12 wherein said detectable label is an enzyme and said determining comprises measuring the activity of said enzyme.

15. The method of claim 14 which further comprises combining in said combining step substrates for said enzyme.

16. The method of claim 14 wherein said enzyme is selected from the group consisting of glucose-6-phosphate dehydrogenase and alkaline phosphatase.

17. The method of claim 12 wherein said antibody is bound to a support or capable of being bound to a support.

18. A method for a homogeneous immunoassay for mycophenolic acid in a sample suspected of containing said mycophenolic acid which comprises:
   (a) combining in a liquid medium:
      (i) said sample,
      (ii) a conjugate of an analog of mycophenolic acid and an enzyme,
      (iii) a monoclonal antibody capable of distinguishing between mycophenolic acid and a mycophenolate ester, and
      (iv) substrates for said enzyme;
   (b) determining the enzymatic activity of said enzyme in said medium; and
   (c) comparing said activity to the enzymatic activity observed with a sample containing a known amount of said mycophenolic acid to determine the presence and/or amount of said mycophenolic acid in said sample.

19. The method of claim 18 wherein said mycophenolate ester is morpholinoethyl E-6-(1,3-dihydro-4-hydroxy-6-methoxy-7-methyl-3-oxo-5-isobenzofuranyl)-4-methyl-4-hexenoate.

20. The method of claim 18 wherein said enzyme is glucose-6-phosphate dehydrogenase.

21. The method of claim 18 wherein said antibody is bound to a support or capable of being bound to a support.

22. A compound comprising mycophenolic acid bound to an immunogenic protein or an enzyme by replacement of one or more hydrogen atoms.

23. The compound of claim 22 wherein said hydrogen atom is a hydrogen atom of the carboxylate group.

24. The compound of claim 22 wherein said protein is an enzyme selected from the group consisting of a glucose-6-phosphate dehydrogenase and an alkaline phosphatase.

25. A compound of the formula:

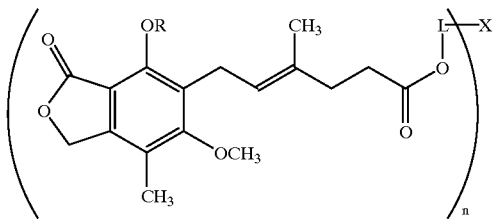

wherein:
X is an immunogenic protein or an enzyme,
L is a bond or a linking group,
R is H, lower alkyl, or CO-lower alkyl, and
n is a number from 1 up to the molecular weight of X divided by 5000.

26. A compound of the formula:

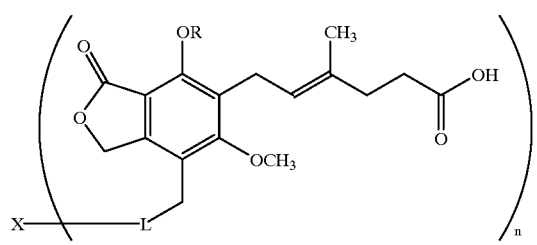

wherein:
X is an immunogenic protein or an enzyme,
L is a bond or a linking group,
R is H, lower alkyl, or CO-lower alkyl, and
n is a number from 1 up to the molecular weight of X divided by 5000.

27. A compound of the formula:

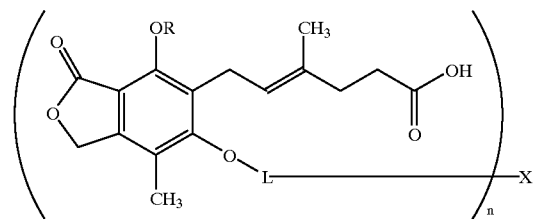

wherein:
X is an immunogenic protein or an enzyme,
L is a bond or a linking group,
R is H, lower alkyl, or CO-lower alkyl, and
n is a number from 1 up to the molecular weight of X divided by 5000.

28. A monoclonal antibody raised in response to a compound comprising mycophenolic acid bound to an immunogenic carrier by replacement of one or more hydrogen atoms wherein said antibody is capable of distinguishing between mycophenolic acid and a compound selected from the group consisting of mycophenolate esters and mycophenolic acid metabolites.

29. The antibody of claim 28 wherein said ester is morpholinoethyl E-6-(1,3-dihydro-4-hydroxy-6-methoxy-7-methyl-3-oxo-5-isobenzofuranyl)-4-methyl-4-hexenoate.

30. The antibody of claim 28 wherein said metabolite is mycophenolic acid glucuronide.

31. A monoclonal antibody that binds mycophenolic acid and is capable of distinguishing between mycophenolic acid and at least one compound selected from the group consisting of morpholinoethyl E-6-(1,3-dihydro-4-hydroxy-6-methoxy-7-methyl-3-oxo-5-isobenzofuranyl)-4-methyl-4-hexenoate, and mycophenolic acid glucuronide.

32. A monoclonal antibody raised to an immunogen selected from the group consisting of:

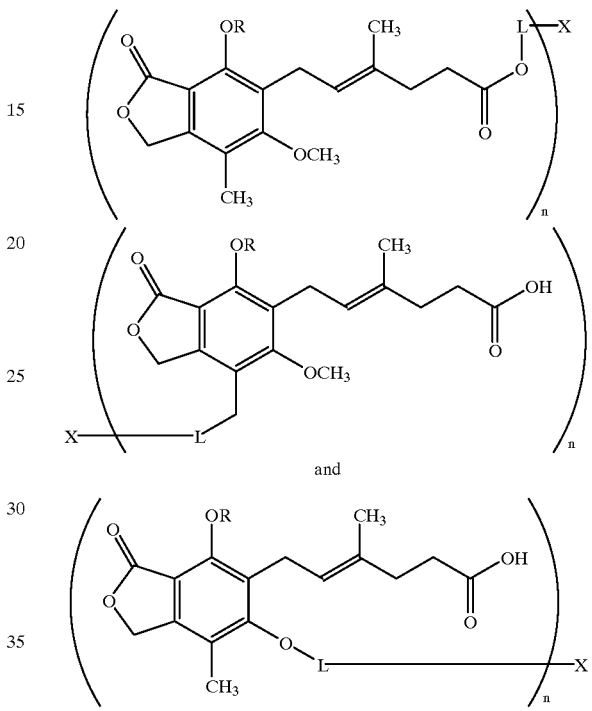

and wherein:
X is an immunogenic carrier,
L is a bond or a linking group,
R is selected from the group consisting of H, lower alkyl, and CO-lower alkyl, and
n is a number from 1 up to the molecular weight of X divided by 5000.

33. A Compound comprising a conjugate of a detectable label and a monoclonal antibody raised in response to the a compound comprising mycophenolic acid bound to an immunogenic carrier by replacement of one or more hydrogen atoms wherein said antibody is capable of distinguishing between mycophenolic acid and a compound selected from the group consisting of mycophenolate esters and mycophenolic acid metabolites.

34. A kit for conducting an assay for the determination of mycophenolic acid, said kit comprising in packaged combination:
(a) a monoclonal antibody capable of distinguishing between mycophenolic acid and mycophenolate esters, and
(b) a compound comprising mycophenolic acid bound to a detectable label.

35. The kit of claim 34 wherein said ester is morpholinoethyl E-6-(1,3-dihydro-4-hydroxy-6-methoxy-7-methyl-3-oxo-5-isobenzofuranyl)-4-methyl-4-hexenoate.

36. A kit for conducting an essay for the determination of mycophenolic acid, said kit comprising in packaged combination:

(a) a monoclonal antibody capable of distinguishing between mycophenolic acid and mycophenolic acid metabolites, and
(b) a compound comprising mycophenolic acid bound to a detectable label.

37. The kit of claim 36 wherein said metabolite is mycophenolic acid glucuronide.

38. A kit for conducting an assay for the determination of mycophenolic acid, said kit comprising in packaged combination:
(a) a monoclonal antibody raised to an immunogen selected from the group consisting of:

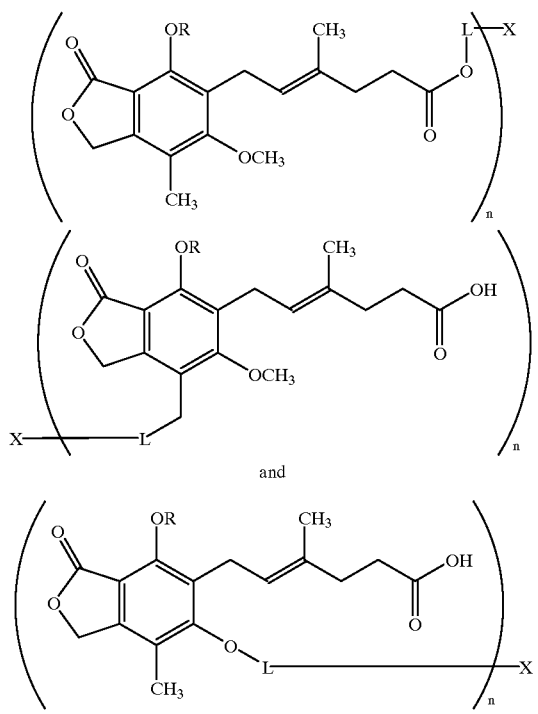

wherein:
X is an immunogenic carrier,
L is a bond or a linking group,
R is selected from the group consisting of H, lower alkyl, and CO-lower alkyl, and
n is a number from 1 up to the molecular weight of X divided by 5000; and (b) a compound selected from the group consisting of:

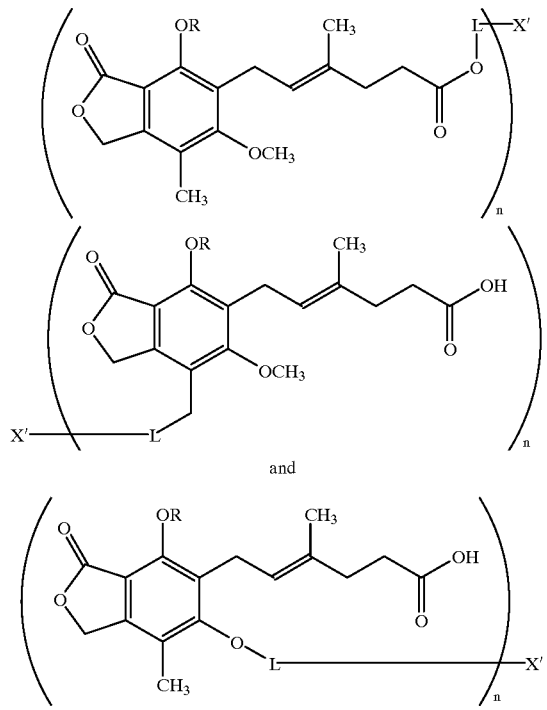

wherein:
X' is a detectable label,
L is a bond or a linking group,
R is selected from the group consisting of H, lower alkyl, and CO-lower alkyl, and
n is a number from 1 up to the molecular weight of X' divided by 5000.

* * * * *